(12) United States Patent
Kamada et al.

(10) Patent No.: US 11,719,920 B2
(45) Date of Patent: Aug. 8, 2023

(54) OBSERVATION ASSISTING DEVICE, INFORMATION PROCESSING METHOD, AND PROGRAM

(71) Applicant: LEICA MICROSYSTEMS (SCHWEIZ) AG, Heerbrugg (CH)

(72) Inventors: Kyosuke Kamada, Hokkaido (JP); Yukie Tamura, Hokkaido (JP); Fumiya Takeuchi, Hokkaido (JP)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 17/089,818

(22) Filed: Nov. 5, 2020

(65) Prior Publication Data
US 2021/0109333 A1    Apr. 15, 2021

Related U.S. Application Data

(63) Continuation of application No. 15/578,528, filed as application No. PCT/JP2016/065272 on May 24, 2016, now Pat. No. 10,852,517.

(30) Foreign Application Priority Data

Jun. 2, 2015    (JP) .................. 2015-112179

(51) Int. Cl.
*G02B 21/00* (2006.01)
*G01J 3/02* (2006.01)
(Continued)

(52) U.S. Cl.
CPC ........ *G02B 21/0012* (2013.01); *G01J 3/0221* (2013.01); *G01J 3/28* (2013.01);
(Continued)

(58) Field of Classification Search
None
See application file for complete search history.

(56) References Cited

U.S. PATENT DOCUMENTS

| 5,329,352 A | 7/1994 | Jacobsen |
| 5,528,368 A | 6/1996 | Lewis et al. |
| (Continued) | | |

FOREIGN PATENT DOCUMENTS

| CN | 104597590 A | 5/2015 |
| JP | H11103471 A | 4/1999 |
| (Continued) | | |

OTHER PUBLICATIONS

Jiang et al., "Gate-controlled generation of optical pulse trains using individual carbon nanotubes," Nature Communications, 2015, vol. 6, 5 pages.

(Continued)

*Primary Examiner* — Derek S. Chapel
(74) *Attorney, Agent, or Firm* — Hodgson Russ LLP

(57) ABSTRACT

Provided are an imaging unit 104 that uses a light emitted from a second beam splitter 202 of a microscope 2 that can use an exciting light and an observation light, which is a light including a wavelength other than that of the exciting light, as a light source by switching there between and is provided with the second beam splitter 202 to image images of the same observation region of the microscope 2 in situations where the exciting light and the observation light are used as the light source and an output unit 106 that overlaps, synthesizes, and outputs the images imaged by the imaging unit 104 respectively using the exciting light and the observation light as the light source.

17 Claims, 6 Drawing Sheets

(51) Int. Cl.
  *G01J 3/28* (2006.01)
  *G02B 27/10* (2006.01)
  *G01N 21/64* (2006.01)
  *G01J 3/00* (2006.01)

(52) U.S. Cl.
  CPC ......... *G01N 21/64* (2013.01); *G01N 21/6458* (2013.01); *G02B 21/0028* (2013.01); *G02B 21/0076* (2013.01); *G02B 27/10* (2013.01); *G01J 2003/003* (2013.01)

(56) References Cited

U.S. PATENT DOCUMENTS

| | | | |
|---|---|---|---|
| 10,852,517 B2 * | 12/2020 | Kamada | ............ G01N 21/6458 |
| 2009/0202119 A1 | 8/2009 | Hefti et al. | |
| 2009/0274360 A1 | 11/2009 | Suzuki et al. | |
| 2010/0145416 A1 | 6/2010 | Kang et al. | |
| 2010/0182418 A1 | 7/2010 | Jess et al. | |
| 2011/0270092 A1 | 11/2011 | Kang et al. | |
| 2012/0016230 A1 | 1/2012 | Kishima et al. | |
| 2012/0057226 A1 | 3/2012 | Kuster | |
| 2013/0041267 A1 | 2/2013 | Ntziachristos et al. | |
| 2014/0378843 A1 * | 12/2014 | Valdes | ................... G02B 21/36 600/476 |

FOREIGN PATENT DOCUMENTS

| | | |
|---|---|---|
| JP | 2000097859 A | 4/2000 |
| JP | 2006171024 A | 6/2006 |
| WO | 0006980 A1 | 2/2000 |
| WO | 2004054439 A2 | 7/2004 |
| WO | 2013109966 A1 | 7/2013 |
| WO | 2014176375 A2 | 10/2014 |

OTHER PUBLICATIONS

Kumamoto et al., "Spontaneous exciton dissociation in carbon nanotubes," Physical Review Letters, 2014, vol. 112, 5 pages.
Sage et al., "Optical magnetic imaging of living cells," Nature, Apr. 2013, vol. 495, 14 pages.
Imamura et al., "Optical control of individual carbon nanotube light emitters by spectral double resonance in silicon microdisk resonators," Applied Physics Letters, Mar. 2013, vol. 102, No. 16, 5 pages.

* cited by examiner (a)

(b)

OBSERVATION ASSISTING DEVICE, INFORMATION PROCESSING METHOD, AND PROGRAM

FIELD

The present invention relates to a device or the like that can be used in diagnosis by being installed to a microscope that can use an exciting light as a light source.

BACKGROUND

Known as a conventional technology is a fluorescent surgical stereo microscope for identifying a fluorescent zone that is an observation target in an observation-target field, configured including: a first illuminating device that, in an excited operating state, irradiates the observation-target field by a light in an exciting wavelength region via at least one illuminating optical line and, in a surgical operating state, irradiates the observation-target field by a light in an illuminating wavelength region via the at least one illuminating optical line; an observation optical line for guiding a reflected light and an emitted light brought about by the observation-target field; and a (preferably selectively insertable) first observation filter in the observation optical line that is transparent in the exciting wavelength region and an emission wavelength region (for example, see patent literature 1).

CITATION LIST

Patent Literature

Patent Literature 1: JP 2012-58732 A (p. 1, FIG. 1, and the like)

SUMMARY OF INVENTION

Technical Problem

However, in the conventional technology, there is a problem where observation cannot be performed appropriately and readily when observing the observation target by the microscope using the exciting light as a light source.

For example, because in observation using the exciting light as the light source only a portion excited by the exciting light can be observed, what is happening in a non-excited portion cannot be confirmed and a situation of the non-excited portion cannot be grasped at the same time. Moreover, in merely observing with the exciting light, it is difficult for a physician or the like to determine whether an appropriate region is being observed.

For example, because in observation using the exciting light as the light source an appearance of an observed region differs greatly from that of a situation where a natural light or the like is used as the light source, it is difficult for the physician or the like to determine whether the appropriate region is being observed and there are also problems such as a positional relationship of a fluorescent portion to a natural-light image being difficult to grasp. That is, consistency with an anatomical position is difficult with a fluorescent image alone and both the fluorescent portion and an anatomical surgical field under the natural light must be grasped at the same time.

The present invention is devised to resolve problems such as above and has as an object to provide an observation auxiliary device or the like that can appropriately and readily perform observation using an exciting light as a light source.

Solution to Problem

An observation auxiliary device of the present invention is an observation auxiliary device provided with an imaging unit that uses a light emitted from a second beam splitter of a microscope that can use an exciting light and an observation light, which is a light including a wavelength other than that of the exciting light, as a light source by switching there between and is provided with the second beam splitter to image images of the same observation region of the microscope in situations where the exciting light and the observation light are respectively used as the light source and an output unit that overlaps, synthesizes, and outputs the images imaged by the imaging unit respectively using the exciting light and the observation light as the light source.

By such a configuration, observation using the exciting light as the light source can be performed appropriately and readily. For example, by overlapping, synthesizing, and outputting the images imaged respectively using the exciting light and the observation light as the light source, a portion that is observable in the image using the observation light but unobservable in the image using the exciting light and an area that is observable in the image using the exciting light and emits a fluorescent light can be observed at the same time. Moreover, for example, observation by the exciting light can be performed while confirming whether an appropriate location is being observed by viewing the portion that is observable with the observation light but unobservable with the exciting light. Moreover, because the image using the exciting light and the image using the observation light are overlapped, synthesized, and output, a correspondence relationship of areas or the like indicated in both images can be grasped readily at a glance. Moreover, because there is no need to move a line of sight between both images, superior visibility is had.

Moreover, the observation auxiliary device of the present invention is the above observation auxiliary device, wherein the microscope is further provided with a first beam splitter, further provided is a spectroscopy unit that splits a light emitted from the first beam splitter of the microscope in the situation where the exciting light is used as the light source, and the output unit further performs outputting according to spectroscopy results by the spectroscopy unit.

By such a configuration, when observing an observation target by the microscope, spectroscopic analysis of the observation region of the microscope can be performed at the same time.

Moreover, the observation auxiliary device of the present invention is the above observation auxiliary device, further provided with an optical fiber to which at least a portion of the light emitted from the first beam splitter becomes incident that emits the incident light to the spectroscopy unit, wherein the spectroscopy unit splits the light incident via the optical fiber from among the light emitted from the first beam splitter.

By such a configuration, when observing the observation target by the microscope, spectroscopic analysis of the observation region of the microscope can be performed at the same time. Moreover, by connecting with the optical fiber, for example, a degree of freedom of the observation auxiliary device—particularly, a position of disposing the spectroscopy unit—can be increased.

Moreover, the observation auxiliary device of the present invention is the above observation auxiliary device, further provided with a reception unit that receives at least one from among an enlargement ratio and a focal length of the microscope, wherein the output unit corrects the spectroscopy results of the spectroscopy unit according to at least one from among the enlargement ratio and the focal length received by the reception unit.

By such a configuration, spectroscopy results corrected for a change in the light incident to the spectroscopy unit due to a change in the enlargement ratio or the focal length can be obtained.

Moreover, the observation auxiliary device of the present invention is the above observation auxiliary device, wherein the microscope has an auto-zoom mechanism and the output unit corrects the spectroscopy results of the spectroscopy unit according to an enlargement ratio of a zoom output by the auto-zoom mechanism.

By such a configuration, correction according to the enlargement ratio of the zoom of the microscope can be performed automatically.

Moreover, the observation auxiliary device of the present invention is the above observation auxiliary device, wherein the output unit performs predesignated outputting in a situation where the spectroscopy results of the spectroscopy unit satisfy predesignated conditions.

By such a configuration, it can be determined whether the observation target observed in the observation region satisfies the predesignated conditions.

Moreover, the observation auxiliary device of the present invention is the above observation auxiliary device, wherein the spectroscopy unit splits a light emitted from the first beam splitter in a situation where normal tissue is observed with the exciting light as the light source and splits a light emitted from the first beam splitter in a situation where abnormal tissue is observed with the exciting light as the light source and the output unit outputs information relating to a comparison between spectroscopy results for the normal tissue and spectroscopy results for the abnormal tissue.

By such a configuration, for example, the spectroscopy results for the abnormal tissue can be analyzed with reference to the spectroscopy results for the normal tissue.

Moreover, the observation auxiliary device of the present invention is the above observation auxiliary device, wherein the spectroscopy unit splits a light emitted from the first beam splitter in a situation of observing the observation target with the observation light as the light source and a light emitted from the first beam splitter in a situation of observing the same observation target with the exciting light as the light source and the output unit uses spectroscopy results of the spectroscopy unit of the situation where the observation light is the light source to correct spectroscopy results of the spectroscopy unit obtained with the exciting light as the light source.

By such a configuration, an influence of the observation light can be removed from the spectroscopy results obtained in the situation where the exciting light is the light source.

Moreover, the observation auxiliary device of the present invention is the above observation auxiliary device, wherein the imaging unit uses a light emitted from the second beam splitter of the microscope to image a plurality of images of the same observation region of the microscope in a situation where the same light source is used and the output unit further outputs an image where the plurality of images imaged by the imaging unit is synthesized.

By such a configuration, the plurality of images can be synthesized to output an image emphasizing a specific portion or the like in the image—for example, a fluorescent portion or the like.

Moreover, the observation auxiliary device of the present invention is the above observation auxiliary device, wherein the output unit further outputs the images imaged by the imaging unit respectively using the exciting light and the observation light as the light source at the same time but without overlapping.

By such a configuration, in addition to the synthesized image, the image of the observation region in the situation where the observation light is the light source and the image of the observation region in the situation where the exciting light is the light source that are not synthesized can be output. By this, for example, the image of the observation region in the situation where the observation light is the light source and the image of the observation region in the situation where the exciting light is the light source can be compared. Moreover, portions displayed in the image with the observation light as the light source and portions displayed in the image with the exciting light as the light source can be viewed clearly separated.

Moreover, the observation auxiliary device of the present invention is the above observation auxiliary device, further provided with a determination unit that, in the situation of using the exciting light as the light source, determines whether the image imaged by the imaging unit is moved or an enlargement ratio of the image is changed, wherein the imaging unit, in a situation where the determination unit detects a movement of the image or a change in the enlargement ratio, switches the light source to the observation light and images an image of the observation region of the microscope and the output unit updates an output of the image imaged by the imaging unit with the observation light as the light source.

By such a configuration, a change in the observation region in the situation of observing using the exciting light can be detected and an imaging image using the observation light as the light source for the changed observation region can be automatically acquired.

Moreover, the observation auxiliary device of the present invention is the above observation auxiliary device, wherein the observation light is a natural light.

By such a configuration, observation using the exciting light as the light source can be performed appropriately and readily. For example, by overlapping, synthesizing, and outputting images imaged respectively using the exciting light and the natural light as the light source, a portion that is observable in an image using the natural light but unobservable in the image using the exciting light and the area that is observable in the image using the exciting light and emits the fluorescent light can be observed at the same time. Moreover, for example, observation by the exciting light can be performed while confirming whether the appropriate location is being observed by viewing the portion that is observable with the natural light but unobservable with the exciting light. Moreover, because the image using the exciting light and the image using the natural light are overlapped, synthesized, and output, a correspondence relationship of areas or the like indicated in both images can be grasped readily at a glance. Moreover, because there is no need to move the line of sight between both images, superior visibility is had.

Advantageous Effects of Invention

According to the observation auxiliary device or the like according to the present invention, observation using an exciting light as a light source can be performed appropriately and readily.

DESCRIPTION OF EMBODIMENTS

Embodiments of an observation auxiliary device and the like are described below with reference to the drawings. Note that because components labeled with the same reference signs in the embodiments perform similar operations, redundant description may be omitted.

Embodiments

Figure 1:
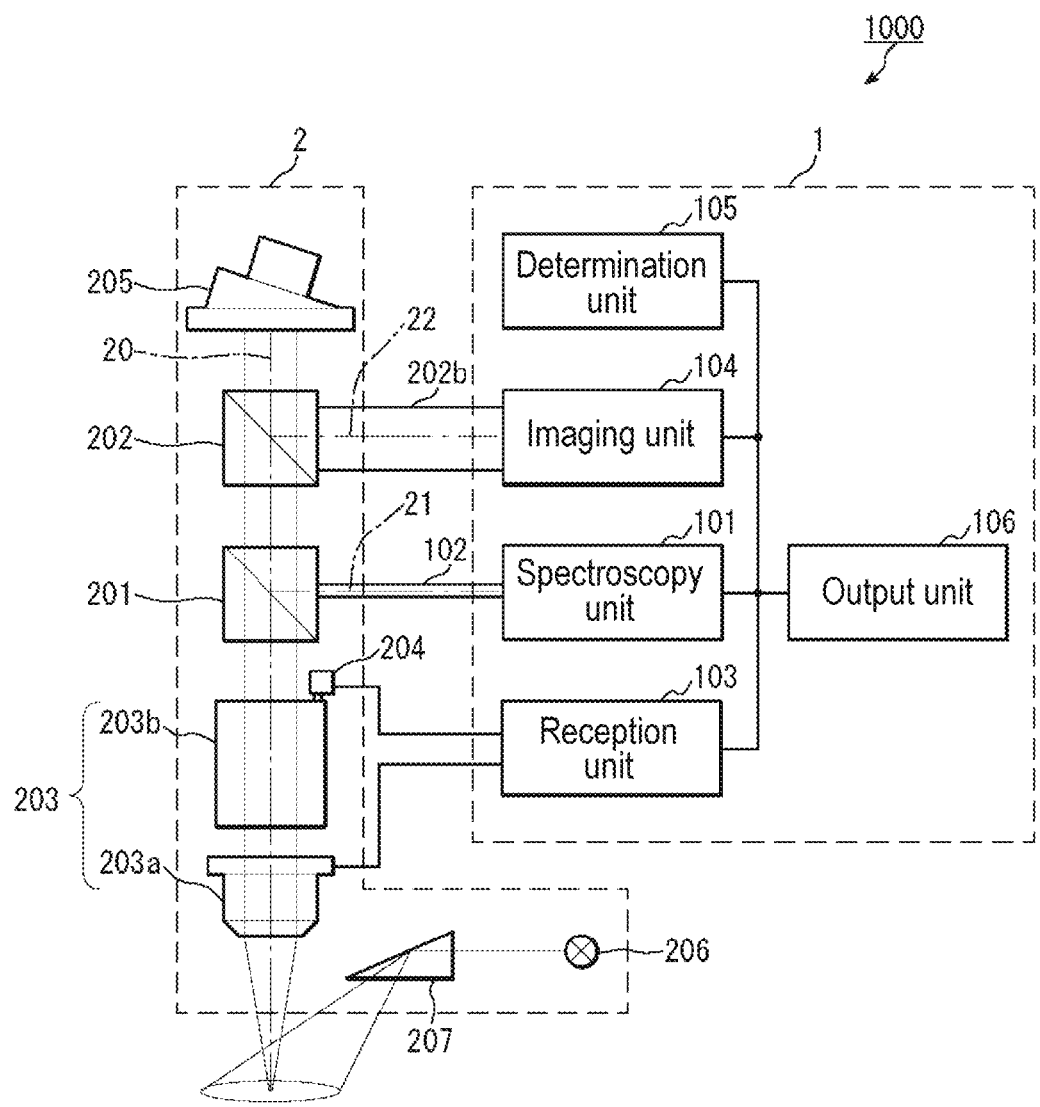
FIG. 1 is a schematic diagram illustrating one example of a configuration of a diagnostic system in an embodiment of the present invention.

FIG. 1 is a schematic diagram illustrating one example of a diagnostic system 1000 in an embodiment of the present invention.

The diagnostic system 1000 is provided with an observation auxiliary device 1 and a microscope 2.

The observation auxiliary device 1 is provided with a spectroscopy unit 101, an optical fiber 102, a reception unit 103, an imaging unit 104, a determination unit 105, and an output unit 106.

The microscope 2 is provided with a first beam splitter 201, a second beam splitter 202, a lens group 203, an auto-zoom mechanism 204, an eyepiece portion 205, a light source 206, and a deflecting prism 207.

The microscope 2 is a microscope that can use an exciting light as the light source. The microscope 2 is, for example, an optical microscope. The microscope 2 is, for example, a surgical stereo microscope. The exciting light is, for example, a light of a wavelength that excites a fluorescent substance accumulated in an observation target. By irradiating the exciting light to a region including a portion accumulated with the fluorescent substance, a fluorescent light can be emitted (radiated) from the portion accumulated with the fluorescent substance and the portion accumulated with the fluorescent substance can be viewed with the microscope.

The microscope 2 is provided with the lens group 203, the first beam splitter 201, the second beam splitter 202, and the eyepiece portion 205 disposed on the same optical line 20 and enables observation from the eyepiece portion 205 of an observation target disposed in a position opposing the lens group 203 via the lens group 203, the first beam splitter 201, and the second beam splitter 202. Here, the same optical line 20 is, for example, an optical line along which a light incident to the lens group 203 from the observation target travels to the eyepiece portion 205. Dispositions of the first beam splitter 201 and the second beam splitter 202 relative to this optical line 20 may be reversed.

The lens group 203 is configured by one or more lenses—normally, a plurality of lenses. Here, as one example, illustrated is a situation where the lens group 203 has an objective lens 203a, disposed on an observation-target side, and a zoom lens 203b. The objective lens 203a is configured by one or more lenses (normally, a plurality of lenses) that are not illustrated. In a situation where the objective lens 203a is configured by the plurality of lenses, a number thereof, a type and combination of the configuring lenses, and the like do not matter.

The zoom lens 203b is configured by a plurality of lenses (not illustrated) and can change a focal length and an enlargement ratio by moving a position of one or more lenses forward and backward. The enlargement ratio may be conceived of as a magnification. Here, the zoom lens 203b can change the enlargement ratio by motorized movement of a position of one or more configuring lenses by the auto-zoom mechanism 204 according to an operation performed by a user on an operation unit that is not illustrated. However, the zoom lens 203b may also be a manually-operable zoom lens. The auto-zoom mechanism 204 may, for example, acquire information indicating a current enlargement ratio of the zoom lens 203b and information of the focal length and the like that is changed by zooming and output these to the observation auxiliary device 1. Note that because a configuration of the auto-zoom mechanism 204 and a configuration whereby the auto-zoom mechanism 204 acquires the information of the enlargement ratio and the like are known, detailed description is omitted here.

Moreover, the objective lens 203a may acquire information of its own focal length, enlargement ratio, and the like and output these to the observation auxiliary device 1. Because a configuration for acquiring the information on the enlargement ratio and the like of the objective lens 203a is known, detailed description is omitted here. This is also the case with, for example, an eyepiece lens (not illustrated) had by the eyepiece portion 205 that is described below.

Note that in the present embodiment, the lens group 203 may be an objective lens configured by, as with the zoom lens, a plurality of lenses having a configuration where a position of a lens can be moved. Moreover, the lens group 203 does not have to have the zoom lens 203b. Moreover, a position where the zoom lens 203b is provided does not matter.

The first beam splitter 201 separates a light incident from the observation target via the lens group 203 in two and emits one of the separated lights to the optical line 20 leading to the eyepiece portion 205 described above. Moreover, it emits the other separated light to the spectroscopy unit 101 of the observation auxiliary device 1. That is, the other separated light is emitted to an optical line 21, which is incident from the first beam splitter 201 to the spectroscopy unit 101. Here, specifically, the separated light is made incident to the optical fiber 102, which is optically connected to the spectroscopy unit 101. In a vicinity of an end face on a first-beam-splitter 201 side of the optical fiber 102, one or more lenses (not illustrated) may be provided for condensing the light separated by the first beam splitter 201 and causing this to become incident to the end face of the optical fiber 102. For example, the first beam splitter 201 separates the light in two by reflecting a portion of the incident light and transmitting the remaining light. Normally, the reflected light is emitted to the spectroscopy unit 101. As the first beam splitter 201, known are, for example, a prism type, a flat type, a wedge-board type, and the like. Here, illustrated as one example is a situation where a first beam splitter 201 of a prism type is used. Note that the first beam splitter 201 may be a half mirror. Note that because a configuration of a beam splitter is known, detailed description is omitted here.

The second beam splitter 202 separates the light incident from the observation target via the lens group 203 and the first beam splitter 201 in two and emits one of the separated lights to the optical line 20 leading to the eyepiece portion 205 described above. Moreover, it emits the other separated light to the imaging unit 104 of the observation auxiliary device 1. That is, the other separated light is emitted to the optical line 21 that is incident from the first beam splitter 201 to the spectroscopy unit 101. The imaging unit 104 and the second beams splitter 202 are connected via a connecting portion 202b that is, for example, a connecting tube, a mounting member, or the like. Between the imaging unit 104 and the second beam splitter 202, one or more lenses (not illustrated) for condensing the light separated by the second beam splitter 202 and causing this to become incident to an imaging face (not illustrated) or the like of the imaging unit 104 may be provided. Because a configuration and the like similar to those of the first beam splitter 201 can be used for a configuration and the like of the second beam splitter 202, detailed description is omitted here.

The microscope 2 is normally provided with two eyepiece portions 205. However, the eyepiece portion 205 may be one in number. The eyepiece portion 205 is provided with, for example, the eyepiece lens (not illustrated).

Note that the microscope 2 may be provided with an optical system of one or more lenses or the like other than the above. For example, an imaging lens (not illustrated), a deflecting prism (not illustrated), and the like may be provided on, for example, the same optical line described above. In a situation where the imaging lens is provided, the first beam splitter 201 and the second beam splitter 202 are each preferably provided between the objective lens 203a and the imaging lens.

Moreover, while description is omitted here, the microscope 2 may be provided with a focus mechanism or the like.

Moreover, the microscope 2 may be provided with, for example, a microscope information output unit (not illustrated) that acquires at least one from among the information of the focal length and the information of the enlargement ratio and outputs this to the observation auxiliary device 1. Note that because a configuration of acquiring and outputting the information of the focal length and the enlargement ratio of the microscope is a known technique, detailed description is omitted here.

The light source 206 irradiates the exciting light to the observation target of the microscope 2. The light source 206 irradiates to the observation target, for example, an exciting light deflected by the deflecting prism 207. The observation target is, for example, a sample. The observation target is specifically, for example, an affected area of a living body where a tumor is arisen. Irradiating the exciting light to the observation target may be conceived of as irradiating the exciting light to an observation region. Note that the light may be directly irradiated from the light source 206 to the observation target without passing through the deflecting prism 207. Moreover, disposed may be one or more lenses (not illustrated), one or more mirrors such as a concave mirror (not illustrated), or the like between the observation target and the light source 206.

The light source 206 may irradiate the light from a surface of the observation target or from a reverse face. For example, in a situation where the microscope 2 is a surgical microscope, the light source 206 irradiates the light from in front of the observation target.

A wavelength of the exciting light irradiated by the light source 206 is a light of a wavelength or a wavelength band that can excite the fluorescent substance had by the observation target and cause fluorescent emission, and this wavelength or wavelength band is determined according to the fluorescent substance that is an excitation target. For example, in a situation where 5-ALA (5-aminolevulinic acid) is administered in a situation where the observation target is a tumor, this 5-ALA accumulates in tumor cells and becomes the fluorescent substance (protoporphyrin IX: PpIX); to cause the fluorescent light to be emitted from this fluorescent substance, for example, an exciting light whose wavelength is 400 nm is used.

In the microscope 2, for example, by lighting the light source 206, the exciting light becomes usable as the light source of the light to be irradiated to the observation target and by turning off the light source 206, a natural light becomes usable as the light source of the light to be irradiated to the observation target. That is, the microscope 2, by switching between lighting and turning off the light source 206, can use the exciting light and the natural light as the light source of the light to be irradiated to the observation target by switching there between. Alternatively, switching between irradiating and not irradiating the light of the light source 206 to the observation target can be performed by changing an irradiation direction of the light source 206 or a position of the deflecting prism 207. Here, the natural light may be conceived of as environmental light, visible light, white light, or the like and does not necessarily have to be sunlight. The natural light may be conceived of as, for example, indoor light emitted by an illumination or the like provided in a room. For example, the natural light may be an illumination light irradiated to the observation target during surgery in an operating room or the like. Note that the microscope 2 may have a light source (not illustrated), a deflecting prism (not illustrated), and the like for irradiating the natural light to the observation target.

The light source 206 may be able to switch intensities of the emitted exciting light. For example, the light source 206 may be configured by a plurality of light sources (not illustrated) that irradiates lights of the same wavelength band; in this situation, it can change the intensity of the emitted light by combinations of on and off in the plurality of light sources.

Note that the microscope 2 may be able to switch, as appropriate, between a situation of using the exciting light as the light source and using the natural light as the light source according to information output by the observation auxiliary device 1—for example, control information. For example, the microscope 2 may be able to switch between lighting and turning off the light source 206 that irradiates the exciting light according to the information output by the observation auxiliary device 1.

Note that the microscope 2 illustrated in FIG. 1 is one example; in the present embodiment, it may be a microscope of another structure as long as it is a microscope provided with functions, a structure, and the like such as above.

The observation auxiliary device 1 is, for example, a device used to assist observation by the microscope 2. The observation auxiliary device 1 is preferably detachably installed to the microscope 2. However, the observation auxiliary device 1 may be fixed in a state of being installed to the microscope 2. The observation auxiliary device 1 is, for example, a device used medically. Being used medically means, for example, being used in medical acts such as diagnosis and surgical lighting, inspection related to medical acts, and the like.

The spectroscopy unit 101 splits the light emitted from the first beam splitter 201 of the microscope 2. For example, the spectroscopy unit 101 splits the light incident via the optical fiber 102 from among the light emitted from the first beam splitter 201. For example, the spectroscopy unit 101 is optically connected to the first beam splitter 201 via the optical fiber 102. The optical fiber 102 may be conceived of as, for example, a portion of the observation auxiliary device 1.

For example, the spectroscopy unit 101 splits the incident light and acquires light intensities for each wavelength. Note that here, as appropriate, wavelength may be conceived of as frequency instead. This is also the case below. The light intensities acquired by the spectroscopy unit 101 are, for example, relative intensities. A unit and the like of the light intensities does not matter. The light intensities may be signal strengths indicating the light intensities. The spectroscopy unit 101 acquires, for example, a spectrum of the incident light. The spectrum is, for example, a spectroscopic spectrum. The spectroscopic spectrum is, for example, a fluorescent spectrum or a reflective spectrum for the observation target. For example, the spectroscopy unit 101 acquires a spectrum of the fluorescent light that is emitted from the fluorescent substance of the observation target by the exciting light irradiated from the light source 206, separated by the first beam splitter 201, and made incident. Moreover, for example, the spectroscopy unit 101 acquires a spectrum of the natural light that is reflected by the observation target, separated by the first beam splitter 201, and made incident. Note that the spectrum acquired by the spectroscopy unit 101 may be, for example, an absorption spectrum or an oscillation spectrum. Note that the light intensities acquired by the spectroscopy unit 101 are, for example, relative intensities. For example, the spectrum acquired by the spectroscopy unit 101 is information having a plurality of wavelengths and relative light intensities associated.

For example, the spectroscopy unit 101 may split the light emitted from the first beam splitter 201 in the situation of observing the observation target with the natural light as the light source and the light emitted from the first beam splitter 201 in the situation of observing the same observation target with the exciting light as the light source 206 and acquire spectroscopy results of each. The spectroscopy results are values of the light intensities for each wavelength or a spectrum. The respective acquired spectroscopy results are accumulated in, for example, a storage unit or the like that is not illustrated. Note that in the situation of performing observation using only the exciting light as the light source, it is preferable to turn off the illumination of the room or the like wherein the microscope 2 is disposed and block light entering the room or the like from the outside. In a situation where observation is performed using the exciting light as the light source without turning off and blocking lights in this manner, the spectroscopy unit 101 performs spectroscopy of both the fluorescent light arising due to the exciting light and the reflected light due to the natural light.

Moreover, the spectroscopy unit 101 may split the light emitted from the first beam splitter 201 in a situation where normal tissue is observed with the exciting light as the light source 206 and split the light emitted from the first beam splitter 201 in a situation where abnormal tissue is observed with the exciting light as the light source 206 and acquire respective spectroscopy results. For example, the spectroscopy unit 101 acquires the spectroscopy results for each tissue by having the user switch between the normal tissue and the abnormal tissue as tissue to serve as the observation target. The tissue is normally tissue of a living body. The abnormal tissue is, for example, tissue of a lesion area. The tissue of the lesion area is tumor tissue. The normal tissue is tissue other than the abnormal tissue. However, the tissues used as the normal tissue and the abnormal tissue are preferably tissues of similar areas—for example, the same organ, proximal areas, or the like—of the same living body—for example, the same subject. The respective acquired spectroscopy results are accumulated in, for example, the storage unit or the like that is not illustrated.

Note that because a configuration of the spectroscopy unit 101, operations whereby the spectroscopy unit 101 performs spectroscopy, and the like are similar to those of a normal spectrometer such as the spectrometer illustrated at the following URL and the like, detailed description is omitted here ("Mini-spectrometer: Raman spectroscopy (Analytical Instrument)|Hamamatsu Photonics," [online], [accessed May 29, 2015], internet <URL: http://www.hamamatsu-.com/jp/ja/product/application/1505/4517/4387/index-.html>."

At least a portion of the light emitted from the first beam splitter 201 becomes incident to the optical fiber 102. Moreover, the optical fiber 102 emits the incident light to the spectroscopy unit 101. All or a portion of the light other than the light emitted to the optical line 20 leading to the eyepiece portion 205 from among the light separated by the first beam splitter 201 may be made incident to the optical fiber 102. For example, only a portion of the light may be condensed by the lens or the like that is not illustrated and made incident to the optical fiber 102. For example, only a light obtained from a region in a portion in the observation region of the microscope 2—preferably, near a center of the observation region—may be made incident to the optical fiber 102. Near the center of the observation region is, for example, a target region including a center position of the observation region and is a region occupying an area 50% or less of the observation region—preferably an area of 7 to 13%. With, for example, the area of 7 to 13%, light of an area similar to that of center-weighted metering of a normal camera is received and light of an appropriate area of the observation region can be received. The observation region of the microscope 2 may be conceived of as, for example, an observation field, a field of view, or the like of the microscope 2.

The reception unit 103 receives at least one from among the enlargement ratio and the focal length of the microscope 2. For example, the reception unit 103 may receive information of at least one from among an enlargement ratio and a focal length output by an auto-zoom mechanism 204, an objective lens 203a, an eyepiece portion 205, a microscope information output unit that is not illustrated, or the like of a microscope 2 such as that above. Moreover, received may be information output by the auto-zoom mechanism 204, the objective lens 203a, the eyepiece portion 205, the microscope information output unit that is not illustrated, or the like of the microscope 2 such as above indicating a lens being used by the microscope 2, a situation of the zoom lens, and the like and the reception unit 103 may calculate the information of the enlargement ratio and the focal length using this received information; such a situation may also be conceived of as receiving, substantially, at least one from among the enlargement ratio and the focal length. Moreover, accepted may also be information on the enlargement ratio and the focal length that the user inputs via an input device or the like that is not illustrated. The enlargement ratio of the microscope 2 is similar to an enlargement ratio (or a magnification) of a normal microscope and is, for example, a product of an enlargement ratio of the lens group 203 of the microscope 2 and an enlargement ratio of the eyepiece lens (not illustrated) had by the eyepiece portion 205. Note that because a calculation method and an acquisition method of the enlargement ratio and the focal length of the microscope 2 are known techniques, detailed description is omitted here. Here, reception is a concept that includes reception that is input of information via an input interface (not illustrated), reception of information input from an input device such as a keyboard and mouse or a touch panel, and the like. An input means may be any means, such as one by a numeric keypad, a keyboard, a mouse, or a menu screen. The reception unit 103 can be realized by a device driver of the input means such as the numeric keypad or the keyboard, control software of the menu screen, or the like.

The imaging unit 104 uses the light emitted from the second beam splitter 202 of the microscope 2 to image images of the same observation region of the microscope 2. The imaging unit 104 is provided with an imaging element (not illustrated) such as a CCD or a CMOS. A pixel count, a size, and the like of the imaging element provided by the imaging unit 104 do not matter. The images imaged by the imaging unit 104 are normally color images but may be complaint-Rohm images. The images imaged by the imaging unit 104 may be moving images, still images, or both. The imaging unit 104 may image two or more still images in succession every certain or indefinite time interval. For example, the imaging unit 104 splits the light that is emitted from the second beam splitter 202 and incident via the connecting tube, mounting member, or the like that is not illustrated. For example, the imaging unit 104 is optically connected to the second beam splitter 202 via the connecting tube, the mounting member, or the like. One or more lenses, mirrors, prisms, or the like that are not illustrated may be provided as appropriate between the imaging unit 104 and the second beam splitter 202.

The imaging unit 104 may, for example, use the light emitted from the second beam splitter 202 of the microscope 2 to image a plurality of images of the same observation region of the microscope 2. For example, the imaging unit 104 may image images of the same observation region a plurality of times in succession every predesignated time interval to image the plurality of images of the same observation region of the microscope 2. Moreover, this plurality of images may be a plurality of successive frame images of a moving image imaging the same observation region or a plurality of frame images sequentially acquired every predesignated number of frame images that is one or more from among the moving image. For example, the imaging unit 104 may acquire a moving image and acquire such a plurality of frame images from this moving image. A plurality of images of the same observation region is, for example, a plurality of images imaged without moving the observation region and without making a change in the enlargement ratio or the like with regard to the observation region. For example, the imaging unit 104 may image a plurality of images in a situation where a reception unit that is not illustrated receives an instruction to image a plurality of images of the same observation region or may always image a plurality of images.

Moreover, the imaging unit 104 may use the light emitted from the second beam splitter 202 of the microscope 2 to image images of the same observation region of the microscope 2 in situations where the exciting light and the natural light are respectively used as the light source 206. The images of the same observation region are, as above, images imaged without moving the observation region and without changing the enlargement ratio. With the images imaged here, both may be still images, both may be moving images, or one may be a still image and the other a moving image.

Moreover, the imaging unit 104, in a situation where the determination unit 105, which is described below, detects a movement of an image or a change in the enlargement ratio, may switch the light source to the natural light and image an image of the observation region of the microscope 2. Images to serve as detection targets of the movement or the change in the enlargement ratio are, for example, a moving image imaged using the exciting light as the light source or two or more still images—preferably two or more successive and sequentially-shot still images. Movement of the image is, for example, movement of an imaging target in the images, movement of corresponding pixels or pixel groups, or movement of a corresponding moving object. This is also the case for the change in the enlargement ratio. Moreover, here, movement of the images may be due to movement of the observation region accompanying movement or the like of the microscope 2 or may be due to movement of the observation target. This is also the case for the change in the enlargement ratio. Here, the movement of the images and the change in the enlargement ratio are movement of the images and a change in the enlargement ratio at or above a threshold. For example, in a situation where an image using the exciting light as the light sources is being imaged, the imaging unit 104 may, in a situation where the determination unit 105 that is described below detects the movement of the images or the change in the enlargement ratio, temporarily switch the light source to the natural light and image an image of the observation region of the microscope 2 and, after imaging, switch the light source back to the exciting light and image an image of the observation region of the microscope 2. By this, in a situation where there is a change in a setting of the observation region, an image can be acquired where the changed observation region is imaged by the natural light and an image can be acquired where the changed observation region is imaged by the natural light.

The determination unit 105, in the situation where the exciting light is used as the light source 206, determines whether the images imaged by the imaging unit 104 are moved or whether the enlargement ratio of the images imaged by the imaging unit 104 is changed. For example, the determination unit 105 determines whether the images are moved or the enlargement ratio of the images is changed in a moving image imaged using the exciting light or two or more still images—preferably two or more successive and sequentially-imaged still images—imaged using the exciting light. For example, movement detection is performed for pixels or a pixel group such as a pixel block or a pixel object using image differencing or the like between frame images of the moving image or between the two or more still images and the movement of the images or the change in the enlargement ratio of the images is detected from this movement. For example, in a situation where the movement detected for the pixels or the pixel group is at or above the threshold, it is determined that the image is moved. Moreover, in a situation where a change in a size of the pixel group or the moving object detected by the movement detection—for example, a change in an area—is at or above the threshold, it is determined that the enlargement ratio of the images is changed. Note that because processing to detect the movement of the image and a presence or absence of change in the enlargement ratio of the images from the imaged image is, as a technique of, for example, detecting movement or the like of a subject, a known technique, detailed description is omitted here.

The output unit 106 performs outputting according to the spectroscopy results by the spectroscopy unit 101. The output unit 106 outputs, for example, the spectroscopy results by the spectroscopy unit 101. For example, the output unit 106 outputs in a graph or a table the values of the light intensities for each wavelength the spectroscopy unit 101 acquires as the spectroscopy results. For example, the output unit 106 displays the values of the light intensities for each wavelength in a graph whose horizontal axis is wavelength and whose vertical axis is light intensity. For example, the output unit 106 may set a reference value using light intensities of a wavelength band (range of wavelengths) predesignated from among the light intensities for each wavelength acquired as the spectroscopy results and, as the light intensities acquired for wavelengths other than this wavelength band, output values acquired with this reference value as a reference. The values of the light intensities acquired with the reference value as the reference are, for example, values of light intensities represented by a difference between the light intensities for each wavelength acquired by the spectroscopy unit 101 and the reference value. For example, the output unit 106 may calculate and output light intensities for each wavelength of a situation where the light intensity corresponding to the set reference value is made to be 0. The reference value is set according to the light intensities of the predesignated wavelength band. The predesignated wavelength band is, for example, preferably a wavelength band where it is conceivable that there is no large difference in light-intensity values between the spectroscopy results for the abnormal tissue and the spectroscopy results for the normal tissue. The predesignated wavelength band is, for example, a wavelength band set in a range of 500 to 530 nm. For example, the output unit 106 is an average value, an intermediate value, or the like of the light intensities acquired for the wavelengths included in the predesignated wavelength band from among the spectroscopy results. However, the reference value may be acquired in any manner from the wavelengths included in the predesignated wavelength band.

Moreover, the output unit 106 may use the values of the light intensities for each wavelength acquired as the spectroscopy results by the spectroscopy unit 101 to detect a wavelength at which the light intensity reaches a maximum value and output a value of this wavelength as the output according to the spectroscopy results. Here, the maximum value may be a maximum value in the predesignated wavelength band—that is, within a range of wavelengths. For example, it may be a maximum value in a range where the wavelengths are 550 to 750 nm. Moreover, the value of the light intensity of this maximum value may be acquired and output as the output according to the spectroscopy results. Moreover, an area of a vicinity of the wavelength at which the light intensity is maximal in this graph may be calculated and output. This area may be calculated in any manner and may be, for example, calculated using integration or the like. Moreover, the output unit 106 may detect two or more peaks using the values of the light intensities for each wavelength acquired as the spectroscopy results by the spectroscopy unit 101 to calculate and output a ratio of these peak light-intensity values. Because a technique of automatically detecting the peaks is known, detailed description is omitted here. Note that here, as the light intensities, the values of the light intensities acquired by the spectroscopy unit 101 may be used or a difference between light intensities indicated by spectroscopy results such as above and the reference value may be used. This is also the case below.

Moreover, the output unit 106 may correct the spectroscopy results of the spectroscopy unit 101 according to at least one from among the enlargement ratio and the focal length received by the reception unit 103. Here, correction may be performed for an entirety of the spectroscopy results or a portion thereof. Moreover, the output unit 106 may perform outputting according to the corrected spectroscopy results. Specifically, the light-intensity values of one or more wavelengths had by the spectroscopy results may be corrected according to at least one from among the enlargement ratio and the focal length received by the reception unit 103. For example, because an amount of light incident to the observation region (for example, the observation field) of the microscope 2 decreases when the enlargement ratio increases (or the focal length increases), the output unit 106 may, as the enlargement ratio increases (or as the focal length increases), continuously or discontinuously increase the light-intensity values of the one or more wavelengths. Here, the one or more wavelengths may be all wavelengths for which the spectroscopy unit 101 acquires light-intensity values or a portion of these wavelengths. For example, only the light intensity of the wavelength at which the maximum-value light intensity is obtained or the light intensities of the wavelengths at which the peak light intensities are obtained may be corrected. Alternatively, only the light intensities of the wavelength at which the maximum-value light intensity is obtained and wavelengths in a vicinity thereof or the light intensities of the wavelengths at which the peak light intensities are obtained and wavelengths in a vicinity thereof may be corrected. Here, the maximum value may be a maximum value in the predesignated wavelength band—that is, within a range of wavelengths.

For example, when the enlargement ratio becomes n times, the light incident from the observation region decreases to $1/n^2$ times; therefore, the output unit 106, when the enlargement ratio becomes n times, corrects the light-intensity values of the one or more wavelengths had by the spectroscopy results to $n^2$ times. For example, the output unit 106 corrects the light-intensity maximum value to $n^2$ times. It is favorable to predesignate the enlargement ratio to serve as reference for n times in this situation. It is favorable to conceive the enlargement ratio of this situation of the enlargement ratio to serve as the reference as 1 time. Note that with regard to the focal length as well, it is favorable to correct the light intensity to compensate for the change in the light amount due to the change in the area of the observation region due to the change in the focal length.

Note that when, for example, the light-intensity maximum value of the spectroscopy results acquired by the spectroscopy unit 101 is defined as $L_1$ and the reference value sought as above is defined as $L_B$, with this maximum value $L_1$, the light intensity is corrected to $n^2$ times according to the n times of the enlargement ratio and the corrected light intensity is made to be $n^2 L_1$ and, with a light intensity $L_X$ of another wavelength X, so the light intensity of this reference value $L_B$ does not change before and after correction, $(n^2 L_1 - L_B) L_X / n^2 L_1$ may be acquired as the corrected value. That is, the light intensities of each wavelength may be corrected so the light intensities of each wavelength of the spectroscopy results are allocated between the corrected maximum value and reference value.

Note that the output unit 106 may correct the spectroscopy results of the spectroscopy unit 101 according to an enlargement ratio of a zoom output by the auto-zoom mechanism 204. For example, information of the enlargement ratio of the zoom—that is, information indicating the enlargement ratio of the microscope 2—may be acquired from the auto-zoom mechanism 204 and performed according to this enlargement ratio may be correction similar to the above correction according to the enlargement ratio.

The output unit 106 may perform predesignated outputting in a situation where the spectroscopy results of the spectroscopy unit 101 in the situation where the exciting light is used as the light source satisfy predesignated conditions. For example, the output unit 106 may determine whether among the light intensities for each wavelength that are the spectroscopy results there exists a light intensity at or above a preset threshold and, in a situation where such exists, determine that the conditions are satisfied and perform the predesignated outputting. Moreover, for example, the output unit 106 may determine whether the maximum value of the light intensities for each wavelength that are the spectroscopy results is a light intensity at or above a preset threshold and, in a situation where such is at or above the threshold, determine that the conditions are satisfied and perform the predesignated outputting. Moreover, for example, the output unit 106 may determine whether the area acquired as above for the maximum value of the light intensities for each wavelength that are the spectroscopy results is at or above a preset threshold and, in a situation where such exists, determine that the conditions are satisfied and perform the predesignated outputting. Note that here, the maximum value, the threshold, and the like of the light intensity may be a maximum value and a threshold of the light intensity acquired by the spectroscopy unit 101 or a maximum value and a threshold of a light intensity acquired with a reference value such as above as reference.

Here, the predesignated output is, for example, an output for notifying an observer or the like that an appropriate observation region is set as the observation region (for example, the observation field) of the microscope 2. Here, the predesignated output is, for example, an output of a predesignated sound, a display of a predesignated image, or a lighting or blinking of a predesignated lamp or the like. The predesignated sound may be, for example, a buzzer sound or an alarm sound or may be a reproduction or the like of a pre-prepared audio file. By outputting the sound, that the conditions are satisfied can be notified without hindering observation by the microscope 2. For example, a liquid-crystal panel of a transmissive type (not illustrated), a transparent panel that can emit light partially, or the like may be provided in the eyepiece portion 205 of the microscope 2 and the output unit 106 may perform predesignated display on this liquid-crystal panel or emit a predesignated light. Note that performing the predesignated outputting may be conceived as adding a predesignated change to the output and is a concept that also includes, for example, ending, in the situation where the conditions are satisfied, an output being output in a situation where the predesignated conditions are not satisfied.

Note that the output unit 106 may determine whether a light-intensity peak exists at a predesignated wavelength or in a predesignated wavelength band in the spectroscopy results by the spectroscopy unit 101 in the situation where the exciting light is used as the light source and, according to determination results, output information indicating whether the observation target is the abnormal tissue. For example, as illustrated in non-patent literature 1 below, because it is known that there exists a peak at 636 nm in tumor tissue in a situation where a light obtained by irradiating an exciting light to an observation target is subjected to spectroscopic analysis using a fluorescent substance PpIX, in a situation where a frequency at which the peak is detected is 636 nm, information indicating that the abnormal tissue is included in the observation region—for example, the sound—may be output. (non-patent literature 1: Kōji Shimatani and one other, "Research on Intraoperative Identification of Brain Tumor by 5-ALA-Induced Fluorometry under Surgical Microscope," [online], [accessed May 26, 2015], internet <URL: http://repository.dl.itc.u-tokyo.ac.jp/dspace/bitstream/2261/20382/1/K-01362-a.pdf>).

Note that the output unit 106 may respectively output corrected spectroscopy results as above and uncorrected spectroscopy results. Moreover, it may respectively output at least one from among corrected spectroscopy results as above and uncorrected spectroscopy results and a predesignated output as above.

The output unit 106 outputs, for example, information relating to a comparison between the spectroscopy results for the normal tissue and the spectroscopy results for the abnormal tissue acquired by the spectroscopy unit 101. The information relating to the comparison is information indicating the spectroscopy results for the normal tissue and the spectroscopy for the abnormal tissue in a comparable manner. For example, the information relating to these spectroscopy results acquired and accumulated by the spectroscopy unit 101 are output at the same time and, preferably, on the same screen. This is, for example, a graph illustrating a graph of the spectroscopy results for the normal tissue and a graph of the spectroscopy results for the abnormal tissue overlapped. Moreover, the information relating to the comparison is information indicating a difference between the spectroscopy results for the normal tissue and the spectroscopy results for the abnormal tissue and is, for example, a graph illustrating value difference for each wavelength.

The output unit 106 may use the spectroscopy results of the situation where the natural light is the light source to correct the spectroscopy results obtained with the exciting light as the light source. Moreover, information according to the corrected spectroscopy results may be output similarly to the above uncorrected spectroscopy results. For example, the output unit 106 may acquire and output a difference between the spectroscopy results obtained with the exciting light as the light source and the spectroscopy results of the situation where the natural light is the light source as the corrected spectroscopy results. For example, the output unit 106 subtracts light intensities for each frequency corresponding to each frequency above indicated by the spectroscopy results of the situation where the natural light is the light source from light intensities for each frequency indicated by the spectroscopy results obtained with the exciting light as the light source and outputs light-intensity values for each frequency obtained by subtraction.

The output unit 106 may, for example, as above, further output an image where the plurality of images of the same observation region imaged by the imaging unit 104 is synthesized. Here, the plurality of images imaging the same observation region is, for example, a plurality of images imaged using the same light source—for example, the light source 206 of the exciting light. For example, the output unit 106 synthesizes the plurality of images imaged by the imaging unit 104. Then, it outputs the synthesized image— for example, displays it on a monitor or the like that is not illustrated. The output unit 106 may, for example, sequentially acquire a plurality of frame images of a predesignated number from a moving image imaging the same observation region, synthesize these frame images each time a predesignated number of frame images is acquired, and sequentially display the synthesized images. In this situation, when, for example, displaying a newly-synthesized image, it is favorable to update the image being displayed immediately before with the newly-synthesized image.

Synthesis of the plurality of images is preferably synthesis where, for example, a portion that is fluorescent due to the fluorescent substance is emphasized or more readily recognized. For example, it is preferably synthesis where a portion with high brightness (bright portion) becomes brighter. For example, synthesis of the plurality of images is an addition average of the plurality of images. Moreover, synthesis of the plurality of images may be a screen synthesis of the plurality of images. Because an addition average and screen synthesis of images are known techniques, detailed description is omitted here. However, synthesis other than the above may be performed. A synthesis method may be able to be set as appropriate by the user.

The output unit 106 may, for example, further output (for example, display) the images imaged by the imaging unit 104 respectively using the exciting light and the natural light as the light source. For example, the output unit 106 may display at the same time the images imaged by the respective light sources. For example, the images imaged by the respective light sources may be displayed at the same time by being disposed in one screen. In this situation, for example, the images may be made to not overlap. Moreover, the output unit 106 may display the images completely overlapped. Completely overlapping is overlapping so four sides, orientations, and angles of the images match. When overlapping, for example, these may be disposed so a transparency of an image disposed on top is set to a value other than 0%—for example, about 50%—so an image disposed below is displayed; moreover, the image disposed on top may be synthesized with the image below in a synthesis mode such as overlay synthesis, screen synthesis, burn-in synthesis, or multiplication synthesis. Moreover, the output unit 106 may, for example, overlap, synthesize, and output the images imaged by the imaging unit 104 respectively using the exciting light and the natural light as the light source and output these images imaged by the imaging unit 104 respectively using the exciting light and the natural light so these do not overlap each other. The output unit 106 may, for example, in a situation where the imaging unit 104 is currently imaging an image (for example, a moving image) using the exciting light as the light source, sequentially display the newest imaged images as the image imaged using the exciting light and display an image where the same imaging region is imaged immediately before with the natural light as the light source accumulated in the storage unit or the like that is not illustrated as the image imaged using the natural light. Moreover, the output unit 106 may, in a situation where the imaging unit 104 is currently imaging an image (for example, a moving image) using the natural light as the light source, sequentially display the newest imaged images as the image imaged using the natural light and display an image where the same imaging region is imaged immediately before with the exciting light as the light source accumulated in the storage unit or the like that is not illustrated as the image imaged using the exciting light. Moreover, the output unit 106 may further output an image where synthesized is a plurality of images of the same observation region of the microscope 2 imaged using the same light source by the imaging unit 104. For example, the output unit 106 may output the image where synthesized is the plurality of images of the same region imaged using the same light source together with the image synthesized by overlapping the images where the same observation region is imaged with the exciting light and the natural light as the respective light sources.

Note that even in the situation where an image (for example, a moving image) is currently being imaged with the exciting light as the light source, by performing imaging with the natural light as the light source sequentially every predesignated certain or indefinite time, each time imaging is performed with the natural light as the light source, the image imaged with the natural light as the light source displayed immediately before may be updated with this image. For example, it is favorable to image one frame image with the natural light as the light source each time the imaging unit 104 images twenty-nine frame images with the exciting light as the light source and for the output unit 106 to sequentially display the frame images imaged with the exciting light as the light source and sequentially update and display the frame image imaged every twenty-nine frames as the image imaged with the natural light as the light source. Moreover, the imaging unit 104 may, for example, perform imaging by irradiating the natural light for a moment each time imaging is performed for a predetermined time (for example, for 20 seconds or the like) with the exciting light as the light source. Note that the imaging unit 104 switches as appropriate the light source used in imaging by, for example, outputting an instruction to switch the light source to the microscope 2.

Moreover, the output unit 106 may, for example, in the situation where the imaging unit 104 images an image with the natural light as the light source 206 according to the detection of the movement of the image or the change in the enlargement ratio by the determination unit 105, update, with this image, the output of the image imaged by the imaging unit 104 with the natural light as the light source 206. Doing so is preferable particularly in a situation where the imaging unit 104 is currently performing imaging using the exciting light as the light source. By this, in a situation where the observation region is changed, the image imaged using the natural light as the light source can be updated and a portion imaged using the exciting light can also be indicated in the image imaged with the natural light.

Note that in a situation where a range of the spectroscopy unit 101 receiving the light via the optical fiber 102 is a range that is a portion of the observation region of the microscope 2 as above, the output unit 106 may display an image indicating the range of the portion where the spectroscopy unit 101 receives the light via the optical fiber 102 in the image of the observation region imaged by the imaging unit 104. For example, an image of an outline or the like illustrating the range may be displayed in the image. Moreover, the output unit 106 may display this image indicating the range of the portion where the spectroscopy unit 101 receives the light via the optical fiber 102 on the liquid-crystal panel of the transmissive type or the like provided to the eyepiece portion 205.

Moreover, the output unit 106 may, when synthesizing the image imaged with the natural light as the light source and the image imaged with the exciting light as the light source, set a brightness of a fluorescent display range (for example, a diseased region or the like) of the image imaged with the exciting light as the light source to a default brightness or manually according to an instruction from the user or the like. Moreover, the output unit 106 may automatically set the brightness of the fluorescent display range of the imaged image so as to be a brightness corresponding to the spectroscopy results of the spectroscopy unit 101. For example, the output unit 106 may set a brightness value of the fluorescent display range so the brightness of the fluorescent display range of the imaged image becomes a value of a predetermined ratio of a value in a vicinity of a maximum value of a fluorescence value indicated by the spectroscopy results acquired by the spectroscopy unit 106. For example, the output unit 106 may set a range of brightness values allocated to the fluorescent display range of the imaged image so a maximum value of the brightness of the fluorescent display range becomes the value of the predetermined ratio of the value in the vicinity of the maximum value of the fluorescence value indicated by the spectroscopy results acquired by the spectroscopy unit 106. The value of the vicinity of the maximum value may be the maximum value. The predetermined ratio is, for example, a value that is 1% or greater but less than 100%.

Outputting is a concept that includes display on a monitor; projection using a projector; printing to a printer; sound output; lighting of a lamp or the like; sending to an external device; accumulating in a recording medium; transfer of processing results to another processing device, another program, or the like; and the like. Here, displaying is a concept that also includes display to a monitor via a wired connection or a wireless connection, display to a monitor of another wirelessly-connected device, and the like.

The output unit 106 may be conceived of as including an output device such as a monitor and a speaker but does not have to be conceived as such. Moreover, the output unit 106 may be provided with a plurality of output devices. This plurality of output devices may include output devices of the same type or output devices of different types. The output unit 106 can be realized by driver software of one or two or more output devices, driver software of an output device and the output device, or the like.

Figure 2:
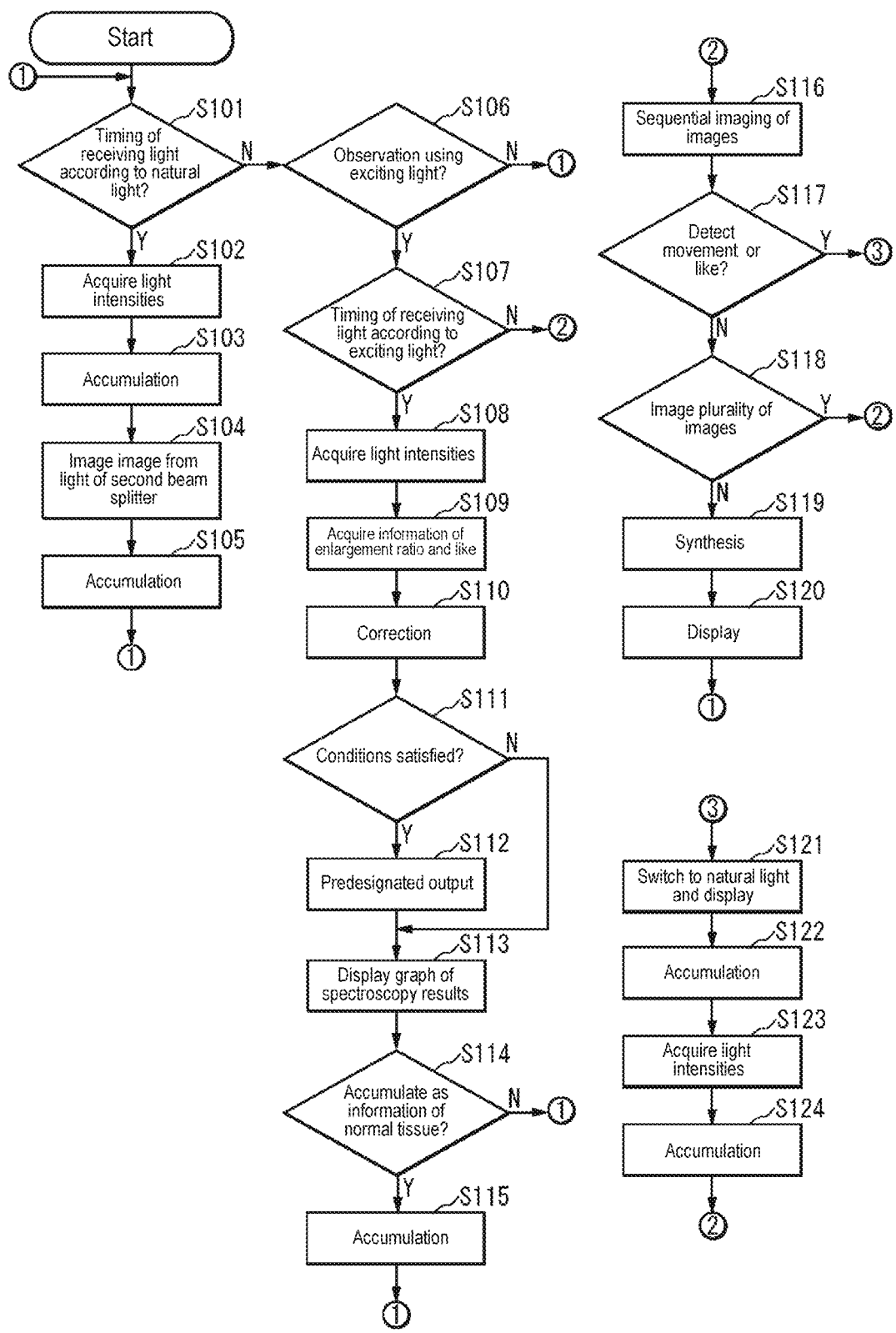
FIG. 2 is a flowchart describing operations of an observation auxiliary device of the diagnostic system.

Next, one example of operations of the observation auxiliary device 1 of the diagnostic system 1000 is described using the flowchart in FIG. 2.

(Step S101) The spectroscopy unit 101 determines whether it is a timing of receiving the light emitted from the first beam splitter 201 of the microscope 2 in the state where the natural light is used as the light source. The timing of reception may be a predesignated specific or indefinite time interval or a timing immediately before observation is performed with the exciting light as the light source. In a situation where it is the timing of reception, the light is received via the optical fiber 102 and the like and the flow proceeds to step S102; in a situation where it is not the timing, the flow proceeds to step S106.

(Step S102) The spectroscopy unit 101 splits the light received at step S101 and acquires the values of the light intensities for each wavelength that are the spectroscopy results.

(Step S103) The spectroscopy unit 101 accumulates the light received at steps S101 in the storage unit or the like that is not illustrated. Note that if the spectroscopy results of the situation where the natural light is used as the light source are unnecessary, the processing of step S102 and step S103 may be omitted.

(Step S104) The imaging unit 104 uses the light output from the second beam splitter 202 to image an image of the imaging region in the situation where the natural light is the light source.

(Step S105) The imaging unit 104 accumulates the image imaged at step S104 in the storage unit that is not illustrated, and the flow returns to step S101.

(Step S106) The spectroscopy unit 101 determines whether observation by the microscope 2 using the exciting light as the light source is performed. For example, in a situation where information indicating that the light source 206 that emits the exciting light was or is lighted is received from the microscope 2, it may be determined that observation using the exciting light as the light source is performed and, in a situation where the reception unit or the like that is not illustrated receives information indicating using the exciting light as the light source from the user, it may be determined that observation using the exciting light as the light source is performed. In the situation where observation using the exciting light as the light source is performed, the flow proceeds to step S107, and in a situation where this is not performed, the flow returns to step S101.

(Step S107) The spectroscopy unit 101 determines whether it is a timing of receiving the light emitted from the first beam splitter 201 of the microscope 2 in the state where the exciting light is used as the light source. For example, the spectroscopy unit 101 determines that it is the timing of reception each time a predesignated time elapses from turning on power or starting the observation auxiliary device 1. In a situation where it is the timing of reception, the light is received via the optical fiber 102 and the like and the flow proceeds to step S108; in a situation where it is not the timing of reception, the flow proceeds to step S116.

(Step S108) The spectroscopy unit 101 splits the light received at step S107 and acquires the values of the light intensities for each wavelength that are the spectroscopy results.

(Step S109) The reception unit 103 receives the information of the enlargement ratio and the focal length from the microscope 2. Moreover, it may read the values of the light intensities for each wavelength acquired and accumulated at step S102 and the like using the natural light as the light source.

(Step S110) The output unit 106, with the information of the enlargement ratio and the focal length acquired at step S109, uses the values of the light intensities for each wavelength acquired using the natural light as the light source to correct the spectroscopy results acquired at step S108.

(Step S111) The output unit 106 determines whether the spectroscopy results corrected at step S110 satisfy the predesignated conditions. For example, it determines whether the maximum value of the light intensities in the predesignated wavelength band (wavelength range) indicated by the spectroscopy results exceeds the predesignated threshold, determining that the conditions are satisfied in a situation where this exceeds the threshold and determining that the conditions are not satisfied in a situation where this does not exceed the threshold. In a situation where it is determined that the conditions are satisfied, the flow proceeds to step S112, and in a situation where it is determined that the conditions are not satisfied, the flow proceeds to step S113.

(Step S112) The output unit 106 performs the predesignated outputting. The predesignated output is, for example, the output of the sound or the lighting of the lamp or the like.

(Step S113) The output unit 106 displays the graph illustrating the spectroscopy results. Note that at step S114 that is described below, in a situation where the information of the spectroscopy results acquired for the normal tissue is accumulated, the graph of the spectroscopy results acquired for this normal tissue may be, for example, displayed overlapped with the above graph of the spectroscopy results. For example, in a situation where the above graph of the spectroscopy results is, for example, the graph of the spectroscopy results acquired for the abnormal tissue, displayed can be the graph comparing the spectroscopy results respectively acquired for the normal tissue and the abnormal tissue.

(Step S114) The output unit 106 determines whether to accumulate the information of the spectroscopy results acquired at step S108 or the spectroscopy results corrected at step S110 as the information of the spectroscopy results acquired for the normal tissue. For example, the output unit 106 determines whether an operation reception unit or the like that is not illustrated receives an instruction from the user or the like to accumulate the information of the spectroscopy results corrected at step S110 as the information of the spectroscopy results acquired for the normal tissue. In a situation of accumulating as the information of the spectroscopy results acquired for the normal tissue, the flow proceeds to step S115, and in a situation of not accumulating, the flow returns to step S101.

(Step S115) The output unit 106 accumulates the spectroscopy results acquired at step S108, the spectroscopy results corrected at step S110, and the like in the storage unit or the like that is not illustrated. The flow then returns to step S101.

(Step S116) The imaging unit 104 uses the light emitted from the second beam splitter 202 of the microscope 2 to sequentially image images of the observation region in the situation where the exciting light is used as the light source. For example, the imaging unit 104 images a moving image of the observation region.

(Step S117) The determination unit 105 performs a process of detecting a movement of the image or a change in the enlargement ratio for the plurality of images (for example, successive frame images configuring a moving image) sequentially imaged by the imaging unit 104 at step S116; in a situation where a movement of the image or a change in the enlargement ratio at or above the predesignated threshold is detected, the flow proceeds to step S121, and in a situation where this is not detected, the flow proceeds to step S118.

(Step S118) The output unit 106 determines whether a plurality of images of the predesignated number is imaged at step S116. In a situation where such is imaged, the flow proceeds to step S119, and in a situation where such is not imaged, the flow returns to step S116.

(Step S119) The output unit 106 synthesizes the plurality of images of the predesignated number from among the plurality of images imaged at step S116. For example, an addition average of the plurality of images is taken to acquire one image.

(Step S120) The output unit 106 displays the image acquired by synthesis at step S119 on the monitor or the like that is not illustrated. For example, the output unit 106 may display the newest image of the observation region imaged using the natural light as the light source on the same screen and at the same time as the image synthesized at step S119. The flow then returns to step S101.

(Step S121) The imaging unit 104 switches the light source of the microscope 2 to the natural light by sending, for example, the instruction to the microscope 2 to switch the light source to the natural light and uses the light emitted from the second beam splitter 202 to image an image of the observation region of the microscope 2 in the situation where the natural light is used as the light source. The image imaged here maybe a still image, a moving image, or one frame image or several successive frame images of a moving image.

(Step S122) The imaging unit 104 accumulates the imaged image in the storage unit or the like that is not illustrated.

(Step S123) The spectroscopy unit 101 receives the light emitted from the first beam splitter 201 in the state where the light source is switched to the natural light via the optical fiber 102 and the like and acquires the light intensities for each wavelength as the spectroscopy results.

(Step S124) The spectroscopy unit 101 accumulates the spectroscopy results acquired at step S123 in the storage unit or the like that is not illustrated. The flow then returns to step S116.

Note that in the flowchart of FIG. 2, processing ends due to turning power off or an interruption of processing ending.

Specific operations of the diagnostic system 1000 in the present embodiment are described below. Here, the description is given using as an example the situation where the microscope 2 is a surgical microscope and this surgical microscope is used in an operating room to observe as the observation target an affected area of a patient orally administered with 5-ALA. Moreover, the wavelength of the exciting light emitted by the light source 206 is made to be 400 nm and the natural light is made to be an illumination in the operating room.

First, the object lens 203a of the lens group 203 of the microscope 2 is moved over the tumor tissue that is the observation target. When the user performs an operation for observation using the natural light as the light source on the operation unit or the like that is not illustrated of the microscope 2, the light source 206 of the microscope 2 is not lighted but a light reflected from the observation target from among the natural light is emitted to the optical line 20 leading to the eyepiece portion 205 via the lens group 203 and the like. From the eyepiece portion 205 of the microscope 2, the observation target, enlarged by the lens group 203 and the like, is observed with the naked eye. By this, the observation target can be observed by the natural light.

The light emitted from the observation target via the lens group 203 is separated in two by the first beam splitter 201. One of the separated lights becomes incident to the optical fiber 102, passes through the optical fiber 102, and becomes incident to the spectroscopy unit 101 of the observation auxiliary device 1.

Moreover, of the lights separated by the first beam splitter 201, the light emitted to the optical line heading toward the eyepiece portion 205 is separated in two by the second beam splitter 202. One of the separated lights becomes incident to the imaging unit 104 of the observation auxiliary device 1.

The spectroscopy unit 101 determines whether it is the timing of receiving the light that is incident in the situation where the natural light is used as the light source. Here, it is determined that, for example, a current time acquired from a clock or the like that is not illustrated is a time indicating the timing of reception when the predesignated time is elapsed from the above operation and the light intensities for each wavelength are acquired from the light incident via the optical fiber 102. These light intensities for each wavelength are the spectroscopy results of the situation where the natural light is used as the light source. The acquired spectroscopy results are accumulated in the storage unit or the like that is not illustrated.

Moreover, the imaging unit 104 uses the incident light to image a still image of the observation region of the microscope 2. This image is an image imaging the observation region using the natural light. The imaged image is accumulated in the storage unit or the like that is not illustrated.

Here, when the illumination of the operating room is turned off and the user performs an operation for observation using the exciting light as the light source on the operation unit or the like that is not illustrated of the microscope 2, the light source 206 irradiates the exciting light, of a predesignated illuminance (for example, 1,800 lux), to the affected area. Here, it is supposed that, for example, the enlargement ratio of the microscope 2 is set to the reference enlargement ratio and the focal length is also set to the reference focal length. By the exciting light being irradiated, the portion accumulated with the fluorescent substance of the tumor tissue that is the observation target emits a fluorescent light. The fluorescent light emitted from the observation target of the microscope 2 is emitted to the optical line leading to the eyepiece portion 205 via the lens group 203 and the like, and the fluorescent light of the observation target enlarged by the lens group 203 and the like is observed by the naked eye from the eyepiece portion 205 of the microscope 2. Moreover, the microscope 2 sends to the observation auxiliary device 1 the information indicating, for example, that observation using the exciting light as the light source is performed. Moreover, the lens group 203 and the like of the microscope 2 sends the information of the current enlargement ratio, focal length, and the like to the observation auxiliary device 1.

The light (fluorescent light) emitted from the observation target via the lens group 203 is separated in two by the first beam splitter 201. One of the separated lights becomes incident to the optical fiber 102, passes through the optical fiber 102, and becomes incident to the spectroscopy unit 101 of the observation auxiliary device 1.

Moreover, of the lights separated by the first beam splitter 201, the light emitted to the optical line heading toward the eyepiece portion 205 is separated in two by the second beam splitter 202. One of the separated lights becomes incident to the imaging unit 104 of the observation auxiliary device 1.

When the reception unit or the like that is not illustrated of the observation auxiliary device 1 receives from the microscope 2 the information that observation using the exciting light as the light source is performed, the spectroscopy unit 101 acquires the light intensities for each wavelength from the light incident via the optical fiber 102.

Moreover, the reception unit 103 receives the information of the enlargement ratio and the like sent from the microscope 2.

Figure 3:
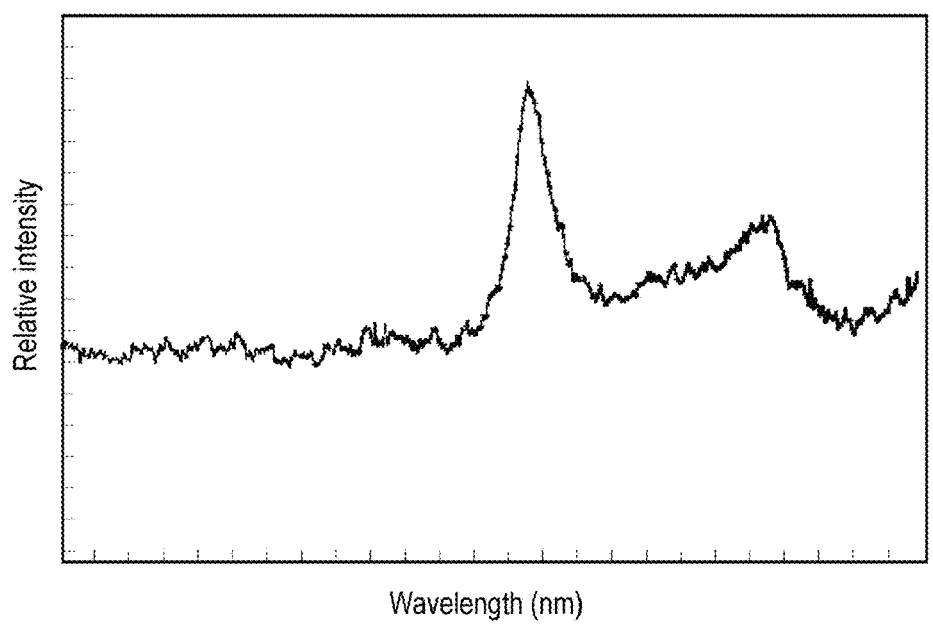
FIG. 3 is a diagram illustrating one example of spectroscopy results acquired by the observation auxiliary device of the diagnostic system.

FIG. 3 is one example of a graph of the spectrum indicating the light intensities for each wavelength acquired by the spectroscopy unit 101. In FIG. 3, the horizontal axis indicates wavelength and the vertical axis indicates light intensity. Here, light intensity is relative intensity.

The output unit 106 acquires the reference value from the light intensities for each wavelength in a range of 500 nm to 520 nm of the spectroscopy results acquired by the spectroscopy unit 101 and acquires the light intensities for each frequency in the situation where the value of the light intensity indicated by this reference value is 0 using the spectroscopy results acquired by the spectroscopy unit 101. Then, an image of the graph illustrating the light intensities for each wave number that are the spectroscopy results acquired in this manner is acquired. Here, as one example, an image of a graph of an approximate curve indicating the light intensities for each wavelength is acquired.

Figure 4:
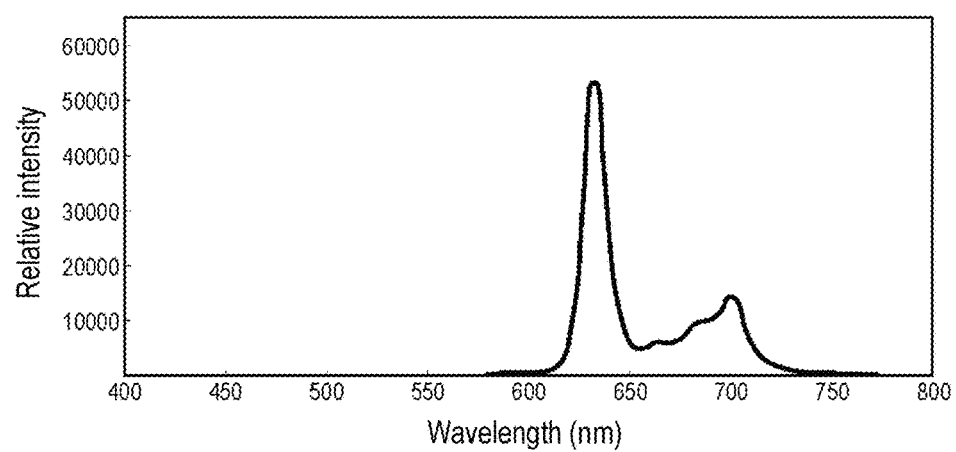
FIG. 4 is a diagram illustrating one example of a graph acquired by the observation auxiliary device of the diagnostic system.

FIG. 4 is a diagram illustrating the image of the graph acquired by the output unit 106. In FIG. 4, the horizontal axis indicates wavelength and the vertical axis indicates light intensity. Here, light intensity is relative intensity.

Note that while the spectroscopic results obtained in the situation where the exciting light is used as the light source may be corrected using spectroscopic results such as above acquired by the spectroscopy unit 101 for the same observation region in the situation where the natural light is used as the light source, here, because the natural light is turned off when performing observation using the exciting light as the light source, the natural light has little effect on observation; therefore, such correction is preset not to be performed.

Moreover, of the spectroscopy results obtained by changing the spectroscopy results acquired by the spectroscopy unit 101 so the value of the light intensity indicated by the reference value is 0, a maximum value of the light intensities in wavelengths of 550 nm to 750 nm is detected. Then, correction is performed as necessary on the detected light intensity. However, here, because the values of the enlargement ratio and the focal length received from the microscope 2 both match the predesignated reference values, correction according to the enlargement ratio and the focal length is not performed. Note that in a situation where the received enlargement ratio and the like differ from the reference values, it is favorable to correct the maximum value according to the difference of the enlargement ratio and the like with regard to this reference value. Moreover, the output unit 106 determines whether the maximum value of the light intensities acquired by the spectroscopy unit 101 (in a situation where correction is performed, the value where the maximum value is corrected) is at or above the preset light-intensity threshold. For example, in a situation of being at or above the threshold, the portion including the fluorescent substance—that is, tumor tissue accumulated with the fluorescent substance—is conceived of as being appropriately disposed in the observation region of the microscope 2. Here, when at or above the threshold, the output unit 106 outputs the predesignated sound. By this sound, the user can recognize that the currently-set observation region is an appropriate observation region while confirming the observation region from the eyepiece portion 205. Note that this sound is preferably only issued when the light intensity that is less than the threshold first becomes equal to or greater than the threshold.

In a situation where no sound is issued, it is conceived that no appropriate observation region is set; therefore, it is favorable for the user to move the observation region of the microscope 2 until the sound is issued to search for the appropriate observation region.

Moreover, the imaging unit 104 images an image of the observation region of the microscope 2 by receiving the light output from the second beam splitter 202. Here, a moving image configured by a plurality of successive frame images is imaged. Then, a plurality of successive frame images of a predesignated number—for example, four successive frame images—is acquired from the imaged frame images and synthesis—here, addition averaging—of the acquired frame images is performed.

Figure 5A:
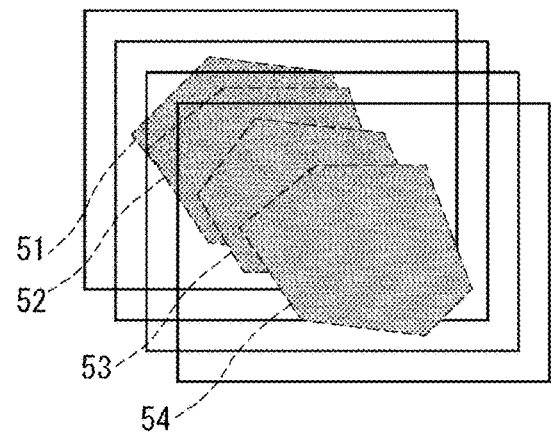
FIG. 5(a) is a schematic diagram illustrating four frame images to serve as synthesis targets and FIG. 5(b) is a schematic diagram illustrating a synthesized image for describing a process of synthesizing a plurality of images by the observation auxiliary device of the diagnostic system.
Figure 5B:
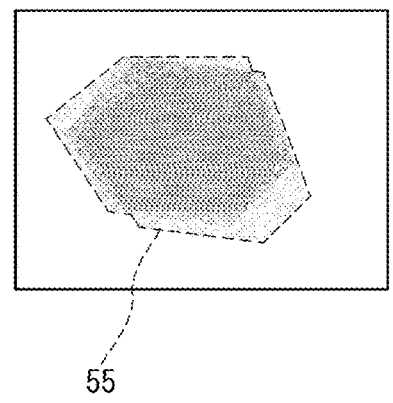

In FIG. 5, (a) is a schematic diagram illustrating the four frame images that are a synthesis target and (b) is a schematic diagram illustrating the synthesized image for describing a process of synthesizing the plurality of images performed by the output unit 106. In the diagram, regions 51 to 54 are the fluorescent portions of each frame image. Moreover, the region 55 is a region in the synthesized image where the fluorescent portions are synthesized.

By performing addition averaging, even in a situation where, for example, a portion of the observation target being observed moves slightly when observation is being performed in the same observation region, pixels of a portion that changed between the plurality of imaged images are averaged between the plurality of images such that values change. Because a portion with no change does not change in value even if averaged, the portion with no change is displayed with emphasis. In a situation where the observation target is a living body, small movements of the observation target due to heart beats, respiration, and the like are unavoidable. However, as illustrated in FIG. 5, by performing addition averaging, among pixels indicating the fluorescent portion, a portion with little change is displayed with emphasis, resulting in an image being obtained where the fluorescent portion is emphasized.

Then, the output unit 106 displays the image obtained by synthesizing the plurality of images imaged with the exciting light as the light source such as that illustrated in (b) of FIG. 5 and the image of the observation region imaged by the imaging unit 104 in the situation where the natural light is the light source in the above at the same time arranged on a monitor 106*a*. Here, for example, the graph of the spectroscopy results illustrated in FIG. 4 is also displayed at the same time.

Figure 6:
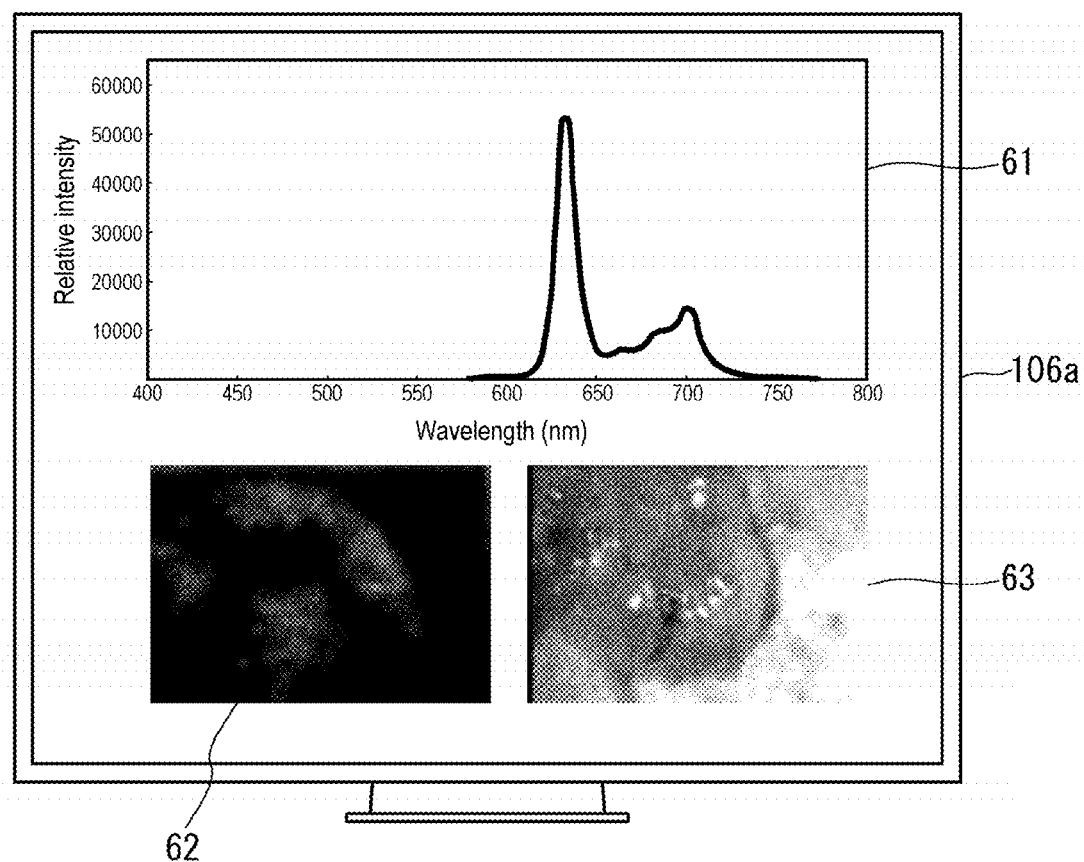
FIG. 6 is a diagram illustrating a display example by the observation auxiliary device of the diagnostic system.

FIG. 6 is a diagram illustrating a display example of the graph illustrating the spectroscopy results by the output unit 106 and the image imaging the observation region: image 61 is the graph illustrating the spectroscopy results, image 62 is the image where the plurality of images imaged in the situation where the exciting light is used as the light source is synthesized, and image 63 is the image where the plurality of images imaged in the situation where the natural light is used as the light source is synthesized.

Note that in a situation where the determination unit 105 determines the presence or absence of a movement of the image or a change in the enlargement ratio between the frame images by performing movement detection or the like as appropriate using the plurality of frame images imaged by the imaging unit 104 when the exciting light is used as the light source and detected is a movement of the image or a change in the enlargement ratio, instead of synthesizing the four successive frame images as above, by turning off the light source 206 of the microscope 2 to switch the light source to the natural light, the imaging unit 104 may image for a moment an image of the observation region with the change and the image of the observation region displayed by the output unit 106 may be updated with this imaged image. Then, by again using the exciting light to image an image of the observation region, in a situation where there is a change in the imaged image, the image imaged using the natural light as the light source and the image imaged using the exciting light as the light source of the observation region after the change can be output—for example, displayed.

Note that the spectroscopy unit 101 and the like are made to perform processing similar to the above and acquire in advance the spectroscopy results of when the normal tissue is observed using the exciting light as the light source and these spectroscopy results are made to be accumulated by the output unit 106 and the like in the storage unit or the like that is not illustrated as the spectroscopy results of the normal tissue according to an operation of the user or the like. Then, when creating a graph illustrating the spectroscopy results of the abnormal tissue such as that illustrated in FIG. 4, created may be a graph overlapped with this graph created from the spectroscopy results of the normal tissue and this graph may be displayed on the monitor 106*a* or the like instead of the graph illustrated in FIG. 4.

Figure 7:
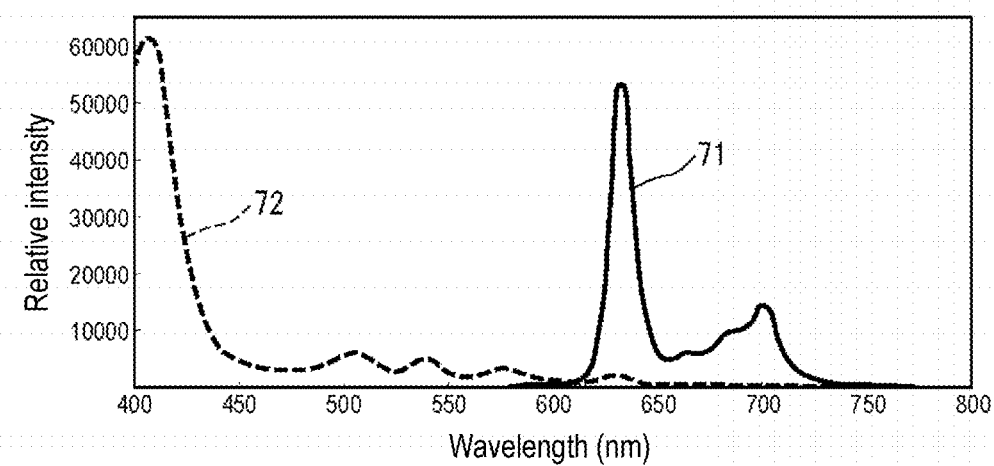
FIG. 7 is a diagram illustrating one example of a graph acquired by the observation auxiliary device of the diagnostic system.

FIG. 7 is a diagram illustrating the graph where the graph illustrating the spectroscopy results of the abnormal tissue and the graph illustrating the spectroscopy results of the normal tissue are overlapped: the solid line 71 is the graph illustrating the spectroscopy results of the abnormal tissue, and the dotted line 72 is the graph illustrating the spectroscopy results of the normal tissue.

As above, according to the present embodiment, when using the exciting light as the light source to observe the observation target by the microscope, spectroscopic analysis of the observation region can be performed at the same time. By this, using the spectroscopic-analysis results, for example, whether the observation region of the microscope 2 is set to an appropriate position can be recognized in real time to perform appropriate observation using the exciting light. Moreover, using the spectroscopic-analysis results, it also becomes possible to, for example, detect in real time abnormal tissue in the observation region.

For example, with the conventional technology, a light amount emitted according to an excited light by a fluorescent substance in a region being observed by a microscope cannot be grasped quantitatively. Therefore, whether being observed is a portion with a large light amount—that is, a portion with a large amount of the fluorescent substance—must be determined subjectively by an observer per se. As a result, there is a problem where it cannot be accurately determined whether an observation region of the microscope is set to a region with the large amount of the fluorescent substance such that appropriate observation cannot be performed and a problem where a long time is required to search for an appropriate observation region. However, according to the present embodiment, by the spectroscopic results, whether an appropriate observation region is being observed and the like can be readily confirmed in real time.

Moreover, with the conventional technology, when performing observation with the microscope, whether the observation target is abnormal tissue cannot be determined using spectroscopy results. For example, to output the spectroscopic results, observation must be stopped temporarily; real-time determination and the like cannot be performed. Therefore, there is a problem where use is inconvenient in a situation of wanting to perform determination in a short time such as a surgery. In contrast, with the present embodiment, using the spectroscopic-analysis results, detection of abnormal tissue in the observation region can be performed in real time, enabling use even in a situation where, for example, a determination is wanting to be made in a short time.

Moreover, with the present embodiment, for example, by overlapping, synthesizing, and outputting the images imaged respectively using the exciting light and the natural light as the light source, an area emitting a fluorescent light can be observed with the image using the exciting light at the same time as confirming whether an appropriate observation location is being observed with the image using the natural light. Moreover, because the image using the exciting light and the image using the natural light are overlapped, synthesized, and output, a correspondence relationship of areas or the like indicated in both images can be grasped readily at a glance. Moreover, because there is no need for the user to move a line of sight between both images, visibility can be improved. By this, in the present embodiment, observation using the exciting light as the light source can be appropriately and readily performed.

Note that in the above embodiment, a situation is described where the exciting light and the natural light are used as the light source, but the present invention can be applied to a situation of using as the light source the exciting light and a light including a wavelength other than that of the exciting light ("observation light"). Because an image imaged using the observation light comes to include a portion not visible in the image imaged using the exciting light, as above, by using the exciting light and the observation light as the light source, it becomes possible to observe at the same time a portion not observable with the exciting light alone by overlapping, synthesizing, and outputting images imaged with each as the light source, enabling observation to be performed appropriately and readily.

The light including the wavelength other than that of the exciting light may be conceived of as a light including at least a light of a wavelength other than the wavelength of the exciting light. The observation light may include the exciting light as long as the light of the wavelength other than that of the exciting light is included but does not have to include the exciting light. The observation light may be a natural light as described in the above embodiment or may include the natural light but does not have to include the natural light. The observation light may be a light of a single color or a light of a plurality of colors. The observation light may include visible light but does not have to include visible light. For example, in a situation where the exciting light is not a red light, the observation light may be a red light or a light including a red light. Moreover, in a situation where the exciting light is a light of a wavelength other than 800 nm, the observation light may be a light of a wavelength of 800 nm, which is a non-visible light. In a situation where, as in this situation, the observation light is a non-visible light, it is preferable to use as the imaging unit or the like an imaging unit provided with a configuration where imaging is possible using a non-visible light as the light source such as an infrared camera.

Note that in each embodiment above, each process (each function) may be realized by undergoing centralized processing by a single device (system) or realized by undergoing distributed processing by a plurality of devices.

Moreover, in the above embodiment, information relating to the processing executed by each component—for example, information received, acquired, selected, generated, sent, and received by each component; information of thresholds, formulas, addresses, and the like used in processing by each component; and the like—may be held temporarily or long-term in a recording medium that is not illustrated even in a situation not specified in the above description. Moreover, accumulation of this information in the recording medium that is not illustrated may be performed by each component or an accumulation unit that is not illustrated. Moreover, reading of the information from this recording medium that is not illustrated may be performed by each component or a reading unit that is not illustrated.

Moreover, in each embodiment above, a situation is described where the observation auxiliary device is a standalone device, but the observation auxiliary device may be a standalone device or a server device in a server-client system. In a situation of the latter, the output unit and the reception unit come to receive input via a communication line and output a screen.

Moreover, in each embodiment above, each component may be configured by dedicated hardware or, for components realizable by software, be realized by executing a program. For example, each component can be realized by a program execution unit such as a CPU reading and executing a software program recorded on a recording medium such as a hard disk or a semiconductor memory. At a time of this execution, the program execution unit may execute the program while accessing a storage unit (for example, a recording medium such as a hard disk or a memory).

Note that the software that realized the observation auxiliary device in each embodiment above is a program such as follows. That is, this program is a program for causing a computer to function as an imaging unit that uses a light emitted from a second beam splitter of a microscope that can use an exciting light and an observation light, which is a light including a wavelength other than that of the exciting light, as a light source by switching therebetween and is provided with the second beam splitter to image images of the same observation region of the microscope of situations where the exciting light and the observation light are respectively used as the light source and an output unit that overlaps, synthesizes, and outputs the images imaged by the imaging unit respectively using the exciting light and the observation light as the light source.

Note that in the above program, functions that can only be realized by hardware are not included in the functions realizable by the above program. For example, functions that can only be realized by hardware such as a modem or an interface card in an acquisition unit that acquires information, an output unit that outputs the information, and the like are not included in the functions realized by the above program.

Moreover, the computer that executes this program may be one in number or a plurality in number. That is, centralized processing or distributed processing may be performed.

Figure 8:
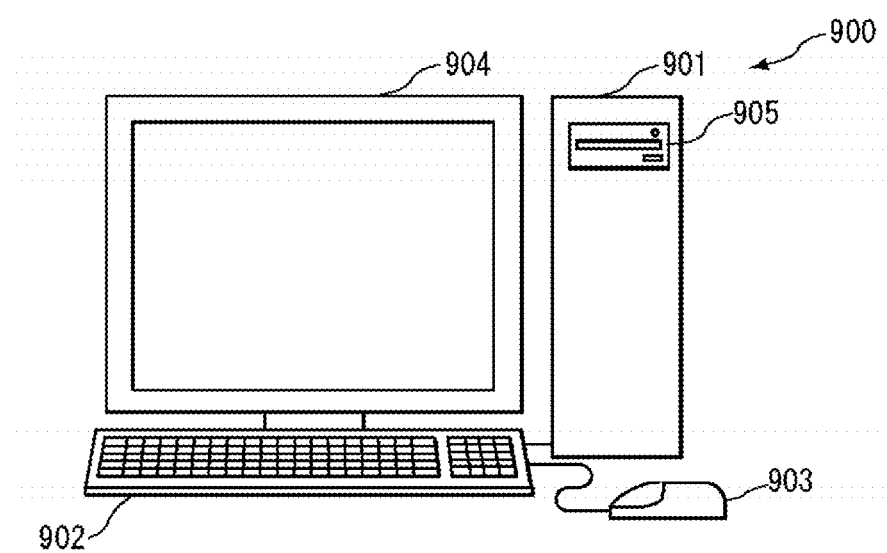
FIG. 8 is a diagram illustrating one example of an appearance of a computer system in an embodiment of the present invention.

FIG. 8 is a schematic view illustrating one example of an appearance of a computer that realizes the observation auxiliary device according to the above embodiment. The above embodiment can be realized by computer hardware and a computer program executed thereon.

In FIG. 8, a computer system 900 is provided with a computer 901 including a CD-ROM (compact disc read-only memory) drive 905, a keyboard 902, a mouse 903, and a monitor 904.

Figure 9:
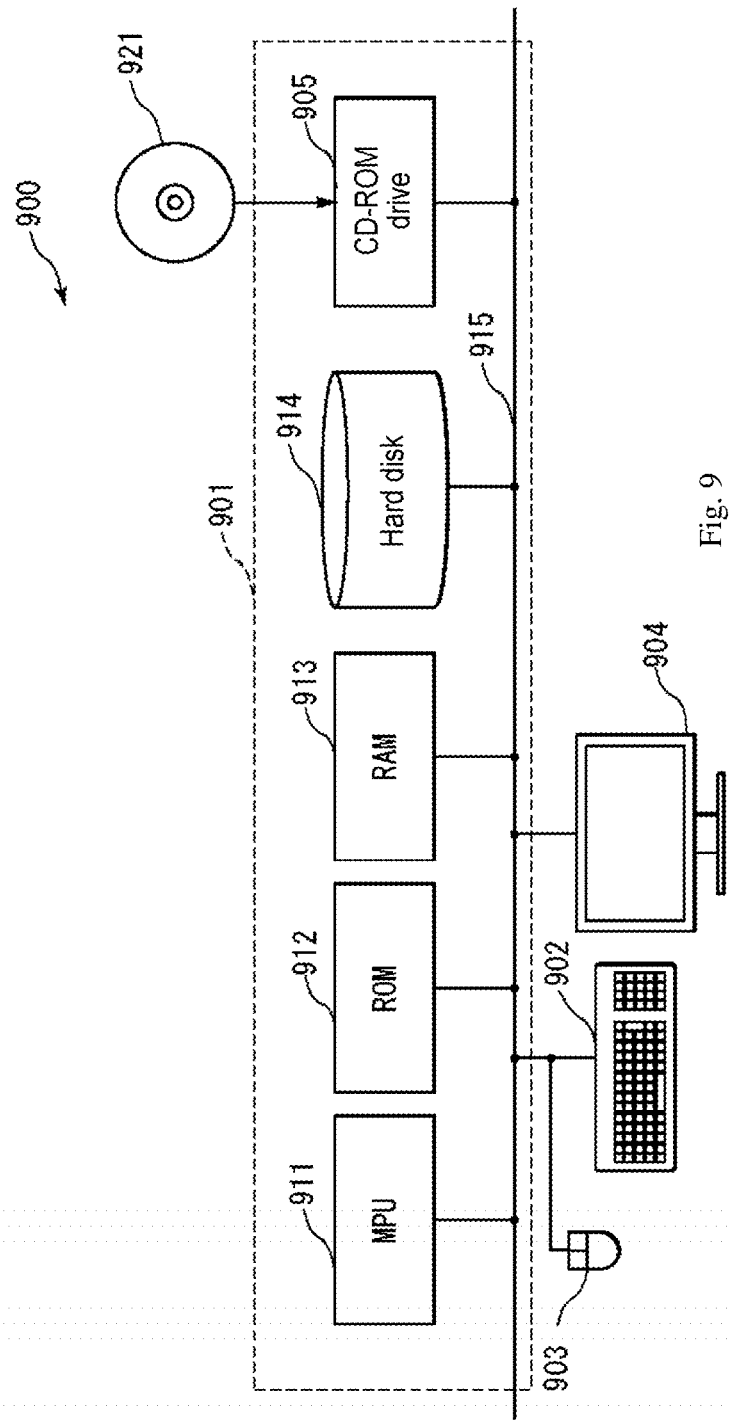
FIG. 9 is a diagram illustrating one example of a configuration of the computer system.

FIG. 9 is a diagram illustrating an internal configuration of the computer system 900. In FIG. 9, in addition to the CD-ROM drive 905, the computer 901 is provided with an MPU (micro processing unit) 911; a ROM 912 for storing a program such as a boot-up program; a RAM (random-access memory) 913 that is connected to the MPU 911, temporarily stores a command of an application program, and provides a temporary storage space; a hard disk 914 that stores the application program, a system program, and data; and a bus 915 that interconnects the MPU 911, the ROM 912, and the like. Note that the computer 901 may include a network card that is not illustrated that provides a connection to a LAN.

A program for causing the computer system 900 to execute the functions of the observation auxiliary device and the like according to the above embodiment may be stored in a CD-ROM 921, inserted in the CD-ROM drive 905, and transferred to the hard disk 914. Alternatively, this program may be sent to the computer 901 via a network that is not illustrated to be stored in the hard disk 914. The program is loaded to the RAM 913 at a time of execution. Note that the program may be loaded from the CD-ROM 921 or directly from the network.

The program does not necessarily need to include an operating system (OS), a third-party program, or the like that causes the computer 901 to execute the functions of the observation auxiliary device according to the above embodiment. The program may call out appropriate functions (modules) in a controlled aspect and only include portions of commands for obtaining desired results. How the computer system 900 operates is known, and detailed description is omitted.

The present invention is not limited to the above embodiments; various modifications are possible, and it is needless to say that such are also included in the scope of the present invention.

INDUSTRIAL APPLICABILITY

As above, the observation auxiliary device according to the present invention is suited as a device or the like that assists observation using a microscope and is particularly useful as a device or the like that splits a light obtained from an observation region of the microscope.

What is claimed is:

1. An observation auxiliary device for use with a surgical microscope operable to use an exciting light and an observation light as a light source by switching between the exciting light and the observation light, wherein the observation light is a light including a wavelength other than a wavelength of the exciting light, and the surgical microscope includes a first beam splitter and a second beam splitter, wherein the second beam splitter receives light from an observation region observed by the surgical microscope, the observation auxiliary device comprising:
   an imaging unit that receives light emitted from the second beam splitter of the surgical microscope and images a plurality of images of the observation region in situations where the exciting light and the observation light are respectively used as the light source;
   an output unit that outputs the images imaged by the imaging unit where the exciting light and the observation light are respectively used as the light source;
   a spectroscopy unit that splits light emitted from the first beam splitter of the surgical microscope and provides spectroscopy results; and
   a reception unit that receives at least one from among an enlargement ratio and a focal length of the surgical microscope;
   wherein the output unit corrects at least a portion of the spectroscopy results of the spectroscopy unit according to at least one from among the enlargement ratio and the focal length received by the reception unit to provide corrected spectroscopy results;
   wherein the output unit further performs outputting according to the corrected spectroscopy results by the spectroscopy unit;
   wherein the spectroscopy unit splits light emitted from the first beam splitter in a situation where normal tissue is observed with the exciting light as the light source and splits light emitted from the first beam splitter in a situation where abnormal tissue is observed with the exciting light as the light source; and
   wherein the output unit outputs information relating to a comparison between spectroscopy results for the normal tissue and spectroscopy results for the abnormal tissue, the information output by the output unit comprising a real-time indication that abnormal tissue is included in the observation region.

2. The observation auxiliary device according to claim 1, further comprising:
   an optical fiber to which at least a portion of the light emitted from the first beam splitter becomes incident that emits the incident light to the spectroscopy unit;
   wherein the spectroscopy unit splits the light incident via the optical fiber from among the light emitted from the first beam splitter.

3. The observation auxiliary device according to claim 2, wherein the correction of at least a portion of the spectroscopy results by the output unit includes adjusting light intensity values of one or more wavelengths in the spectroscopy results.

4. The observation auxiliary device according to claim 1, wherein the surgical microscope has an auto-zoom mechanism, and the output unit corrects the spectroscopy results of the spectroscopy unit according to an enlargement ratio of a zoom output by the auto-zoom mechanism.

5. The observation auxiliary device according to claim 1, wherein the output unit performs predesignated outputting in a situation where the spectroscopy results or the corrected spectroscopy results of the spectroscopy unit satisfy predesignated conditions.

6. The observation auxiliary device according to claim 1, wherein the spectroscopy unit splits light emitted from the first beam splitter in a situation of observing an observation target with the observation light as the light source and light emitted from the first beam splitter in a situation of observing the same observation target with the exciting light as the light source, and the output unit uses spectroscopy results of the spectroscopy unit of the situation where the observation light is the light source to correct spectroscopy results of the spectroscopy unit obtained with the exciting light as the light source.

7. The observation auxiliary device according to claim 1, wherein the imaging unit receives light emitted from the second beam splitter of the surgical microscope to image a plurality of images of the observation region of the surgical microscope in a situation where the same light source is used, and the output unit further outputs an image where the plurality of images imaged by the imaging unit is synthesized.

8. The observation auxiliary device according to claim 1, wherein the output unit further outputs the images imaged by the imaging unit respectively using the exciting light and the observation light as the light source at the same time.

9. The observation auxiliary device according to claim 1, further comprising:
   a determination unit that, in the situation of using the exciting light as the light source, determines whether the image imaged by the imaging unit is moved or an enlargement ratio of the image is changed;
   wherein the imaging unit, in a situation where the determination unit detects a movement of the image or a change in the enlargement ratio of the image, switches the light source to the observation light and images an image of the observation region of the surgical microscope, and the output unit updates an output of the image imaged by the imaging unit with the observation light as the light source.

10. The observation auxiliary device according to claim 1, wherein the observation light is a natural light.

11. The observation auxiliary device according to claim 1, wherein the information relating to the comparison between the spectroscopy results for the normal tissue and the spectroscopy results for the abnormal tissue comprises a graph of spectroscopy results.

12. The observation auxiliary device according to claim 11, wherein the output unit outputs the images imaged by the imaging unit and the graph of spectroscopy results to the same display.

13. The observation auxiliary device according to claim 11, wherein the graph of spectroscopy results illustrates a graph of the spectroscopy results for the normal tissue and a graph the spectroscopy results for the abnormal tissue overlapped.

14. The observation auxiliary device according to claim 11, wherein the graph of spectroscopy results illustrates a graph of a value difference between the spectroscopy results for the normal tissue and the spectroscopy results for the abnormal tissue.

15. A surgical microscope comprising:
 a light source configured to switch between an exciting light and an observation light, wherein the observation light is a light including a wavelength other than a wavelength of the exciting light;
 a first beam splitter and a second beam splitter, wherein the second beam splitter receives light from an observation region observed by the surgical microscope;
 an observation auxiliary device comprising an imaging unit that receives light emitted from the second beam splitter of the surgical microscope and images a plurality of images of the observation region in situations where the exciting light and the observation light are respectively used as the light source;
 an output unit that outputs the images imaged by the imaging unit where the exciting light and the observation light are respectively used as the light source;
 a spectroscopy unit that splits light emitted from the first beam splitter of the surgical microscope and provides spectroscopy results; and
 a reception unit that receives at least one from among an enlargement ratio and a focal length of the surgical microscope;
 wherein the output unit corrects at least a portion of the spectroscopy results of the spectroscopy unit according to at least one from among the enlargement ratio and the focal length received by the reception unit to provide corrected spectroscopy results;
 wherein the output unit further performs outputting according to the corrected spectroscopy results by the spectroscopy unit;
 wherein the spectroscopy unit splits light emitted from the first beam splitter in a situation where normal tissue is observed with the exciting light as the light source and splits light emitted from the first beam splitter in a situation where abnormal tissue is observed with the exciting light as the light source; and
 wherein the output unit outputs information relating to a comparison between spectroscopy results for the normal tissue and spectroscopy results for the abnormal tissue, the information output by the output unit comprising a real-time indication that abnormal tissue is included in the observation region.

16. An information processing method performed using an imaging unit, an output unit, a spectroscopy unit, and a reception unit, comprising:
 an imaging step wherein the imaging unit receives light emitted from a second beam splitter of a microscope, wherein the microscope can use an exciting light and an observation light as a light source by switching between the exciting light and the observation light, wherein the observation light includes a wavelength other than a wavelength of the exciting light, and images a plurality of images of an observation region of the microscope in situations where the exciting light and the observation light are respectively used as the light source;
 an output step wherein the output unit outputs the images imaged by the imaging unit where the exciting light and the observation light are respectively used as the light source;
 a spectroscopy step wherein the spectroscopy unit splits light emitted from a first beam splitter of the microscope and provides spectroscopy results; and
 a reception step wherein the reception unit receives at least one from among an enlargement ratio and a focal length of the microscope;
 wherein the output unit corrects at least a portion of the spectroscopy results of the spectroscopy unit according to at least one from among the enlargement ratio and the focal length received by the reception unit to provide corrected spectroscopy results;
 wherein the output unit performs the output step according to the corrected spectroscopy results by the spectroscopy unit;
 wherein the spectroscopy unit splits light emitted from the first beam splitter in a situation where normal tissue is observed with the exciting light as the light source and splits light emitted from the first beam splitter in a situation where abnormal tissue is observed with the exciting light as the light source; and
 wherein the output unit outputs information relating to a comparison between spectroscopy results for the normal tissue and spectroscopy results for the abnormal tissue, the information output by the output unit comprising a real-time indication that abnormal tissue is included in the observation region.

17. A non-transitory computer readable medium which comprises a stored program for causing a computer to function as
 an imaging unit that receives light emitted from a second beam splitter of a microscope, wherein the microscope can use an exciting light and an observation light as a light source by switching between the exciting light and the observation light, wherein the observation light includes a wavelength other than a wavelength of the exciting light, and that images a plurality of images of an observation region of the microscope in situations where the exciting light and the observation light are respectively used as the light source;
 an output unit that outputs the images imaged by the imaging unit where the exciting light and the observation light are respectively used as the light source;
 a spectroscopy unit that splits light emitted from a first beam splitter of the microscope and provides spectroscopy results; and
 a reception unit that receives at least one from among an enlargement ratio and a focal length of the surgical microscope;
 wherein the output unit corrects at least a portion of the spectroscopy results of the spectroscopy unit according to at least one from among the enlargement ratio and the focal length received by the reception unit to provide corrected spectroscopy results;
 wherein the output unit is further caused to perform outputting according to the corrected spectroscopy results by the spectroscopy unit;
 wherein the spectroscopy unit splits light emitted from the first beam splitter in a situation where normal tissue is observed with the exciting light as the light source and splits light emitted from the first beam splitter in a situation where abnormal tissue is observed with the exciting light as the light source; and wherein the output unit outputs information relating to a comparison between spectroscopy results for the normal tissue and spectroscopy results for the abnormal tissue, the information output by the output unit comprising a real-time indication that abnormal tissue is included in the observation region.

\* \* \* \* \*